United States Patent
Fujikawa et al.

(10) Patent No.: US 8,348,916 B2
(45) Date of Patent: Jan. 8, 2013

(54) INDIVIDUAL PACKAGE AND METHOD OF MANUFACTURING THE SAME

(75) Inventors: Kaori Fujikawa, Kagawa-ken (JP);
Hideki Kondo, Kagawa-ken (JP);
Hitoshi Watanabe, Kagawa-ken (JP);
Masashi Hosokawa, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 649 days.

(21) Appl. No.: 11/736,714

(22) Filed: Apr. 18, 2007

(65) Prior Publication Data

US 2007/0244454 A1  Oct. 18, 2007

(30) Foreign Application Priority Data

Apr. 18, 2006  (JP) ................................. 2006-114809

(51) Int. Cl.
*A61F 13/20* (2006.01)
(52) U.S. Cl. ................ 604/385.02; 604/15; 604/385.13; 604/385.18; 604/904; 383/203; 383/207
(58) Field of Classification Search ............... 604/11–18, 604/385.02, 385.13, 385.18, 904; 383/200, 383/203, 204, 207–211
See application file for complete search history.

(56) References Cited

U.S. PATENT DOCUMENTS

| | | | | |
|---|---|---|---|---|
| 4,620,320 A | * | 10/1986 | Sullivan | ......................... 383/203 |
| 6,773,421 B2 | * | 8/2004 | Bosselaar et al. | ......... 604/385.02 |
| 6,994,696 B2 | * | 2/2006 | Suga | ......................... 604/385.02 |
| 2003/0065300 A1 | | 4/2003 | Suga | |
| 2004/0149613 A1 | | 8/2004 | Mizutani et al. | |
| 2006/0212015 A1 | * | 9/2006 | Peele | ......................... 604/385.13 |
| 2007/0049891 A1 | * | 3/2007 | Clark et al. | ............... 604/385.13 |

FOREIGN PATENT DOCUMENTS

| | | |
|---|---|---|
| CN | 1511021 A | 7/2004 |
| JP | 05-084263 | 4/1993 |
| JP | 2000-279445 | 10/2000 |
| JP | 2000-279446 | 10/2000 |
| JP | 2001-523521 | 11/2001 |
| JP | 2003-104441 | 4/2003 |
| JP | 2003-116914 | 4/2003 |
| JP | 2007-054087 | 3/2007 |
| WO | WO 99/26574 | 6/1999 |
| WO | WO 02/094154 | 11/2002 |

OTHER PUBLICATIONS

Office Action issued to corresponding Chinese Application No. 200780013556.2 mailed Feb. 22, 2012.

* cited by examiner

*Primary Examiner* — Lynne Anderson
(74) *Attorney, Agent, or Firm* — Brinks Hofer Gilson & Lione

(57) ABSTRACT

An individual package is provided to allow a tampon with an applicator to be handled easily. An individual package includes: a tampon including an applicator having an external cylinder and an internal cylinder, and an absorbent body housed so as to be pushed out from the applicator; and a flat bag formed by a predetermined sheet member in a elongated shape. The flat bag includes an unsealable portion formed on one side of the flat bag so as to enable the tampon to be removed therefrom; and a lid portion which is openable and closable in a longitudinal direction of the flat bag. The lid portion is disposed so as to cover the unsealable portion.

9 Claims, 19 Drawing Sheets

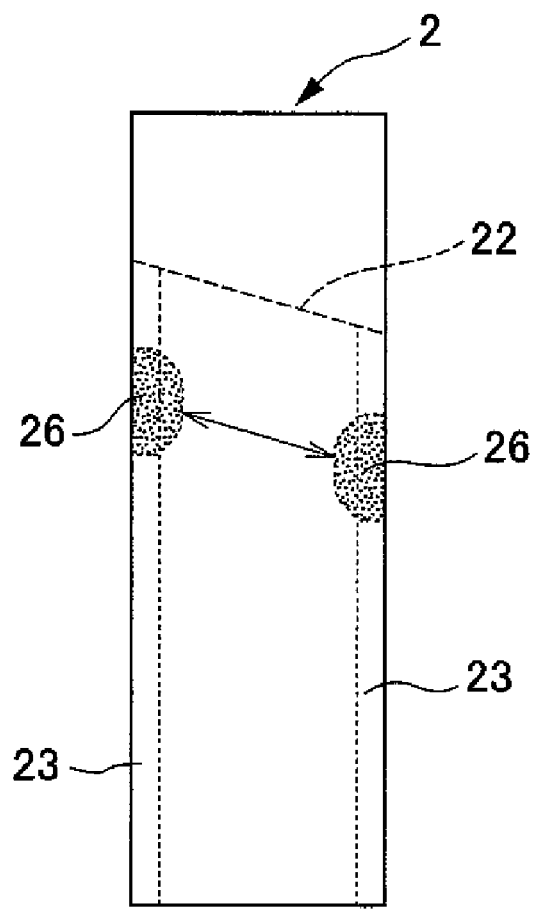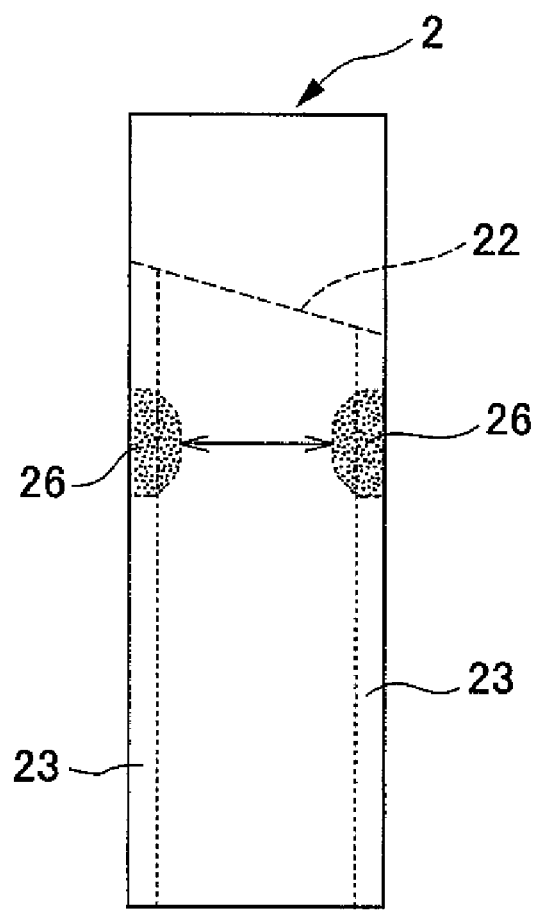

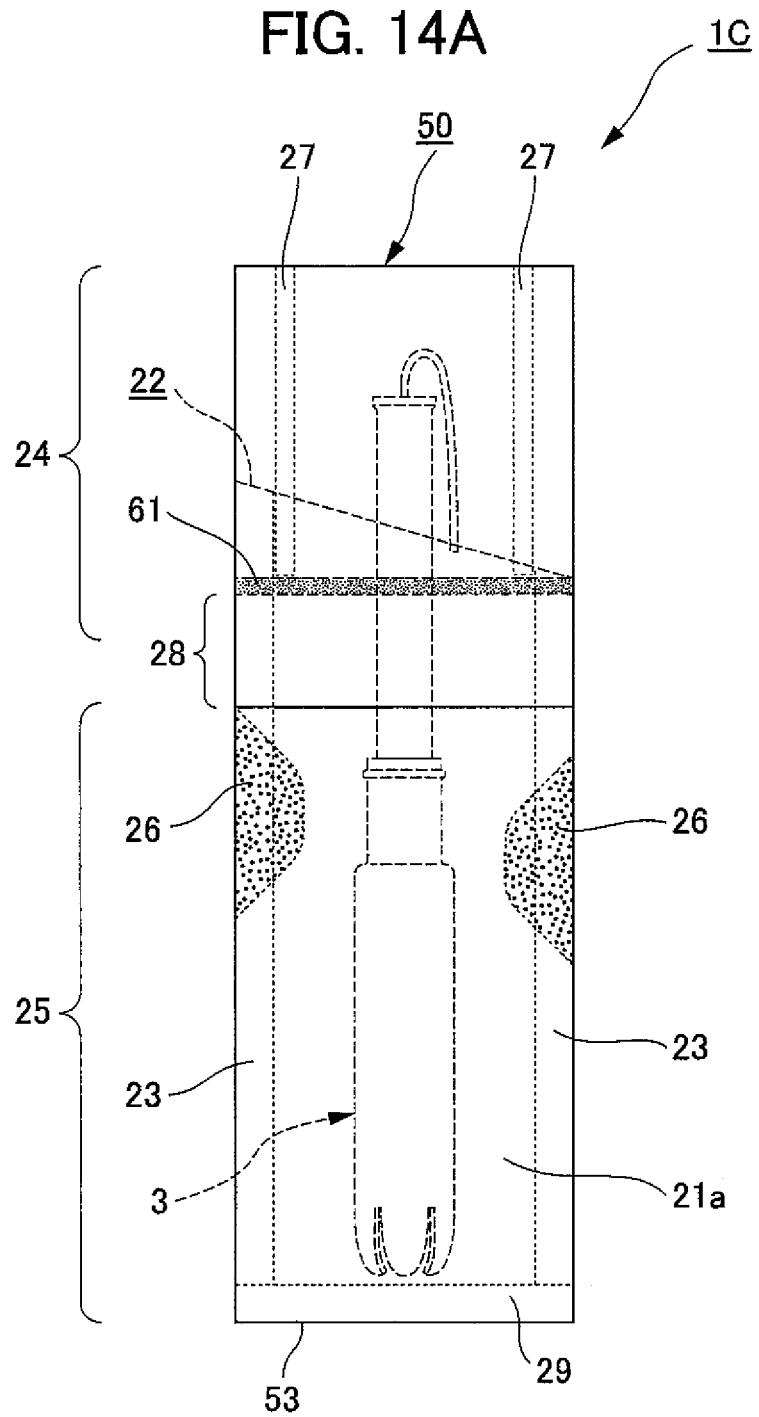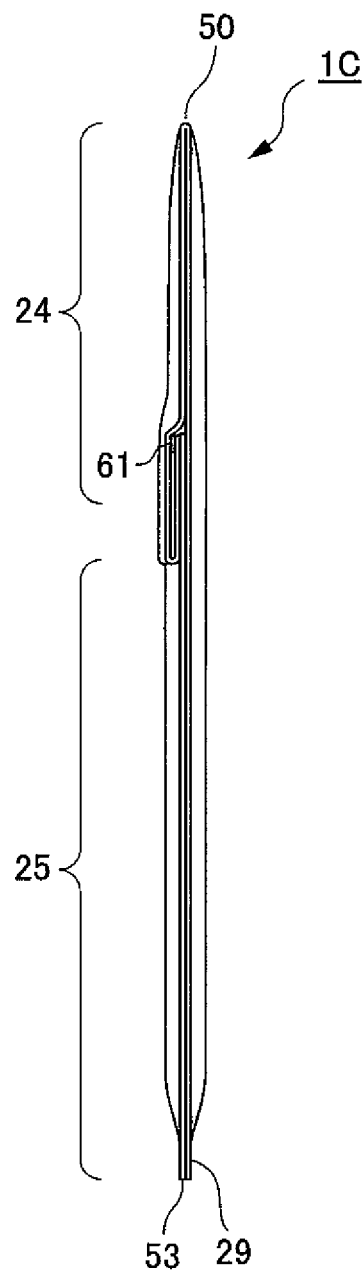

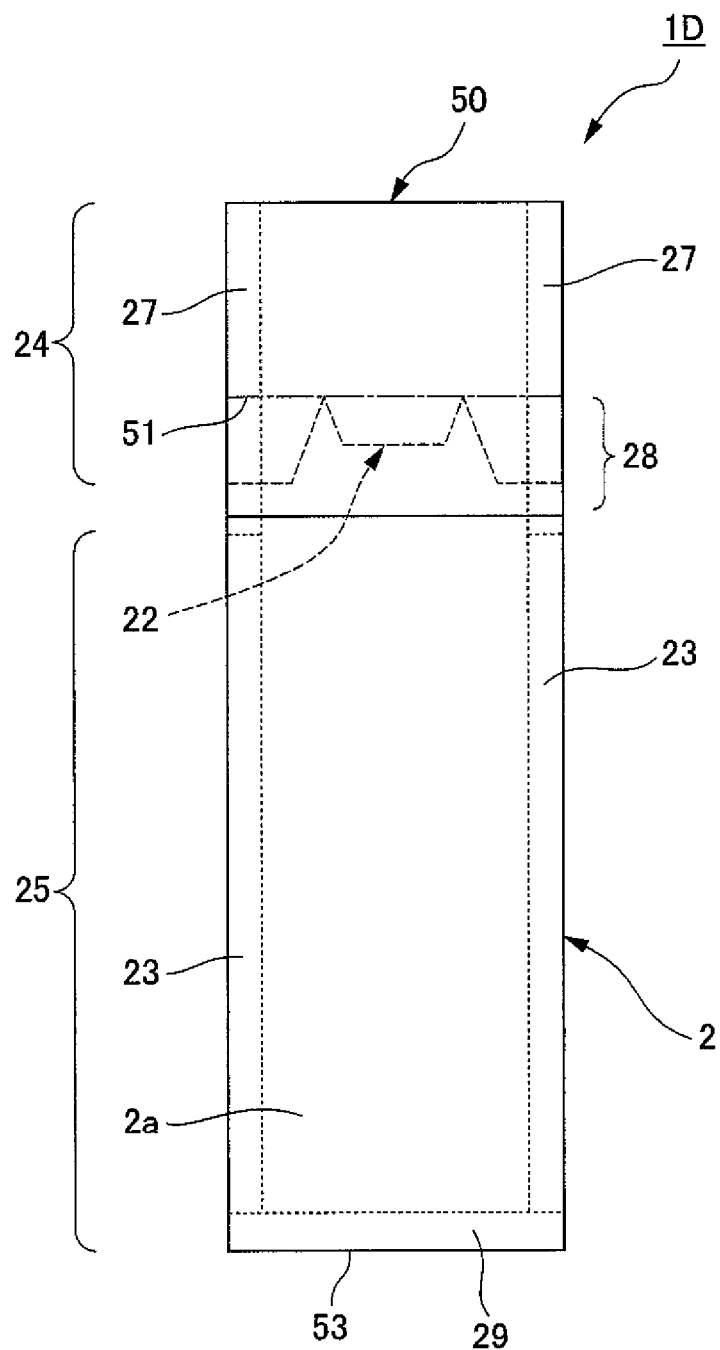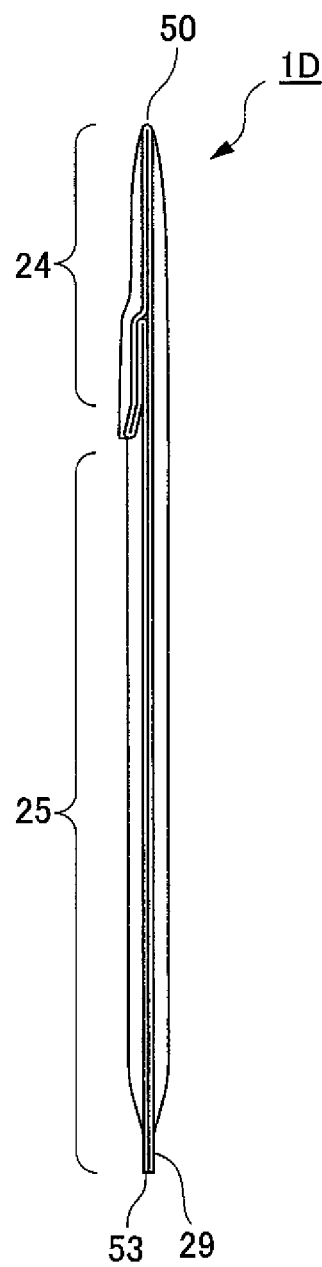

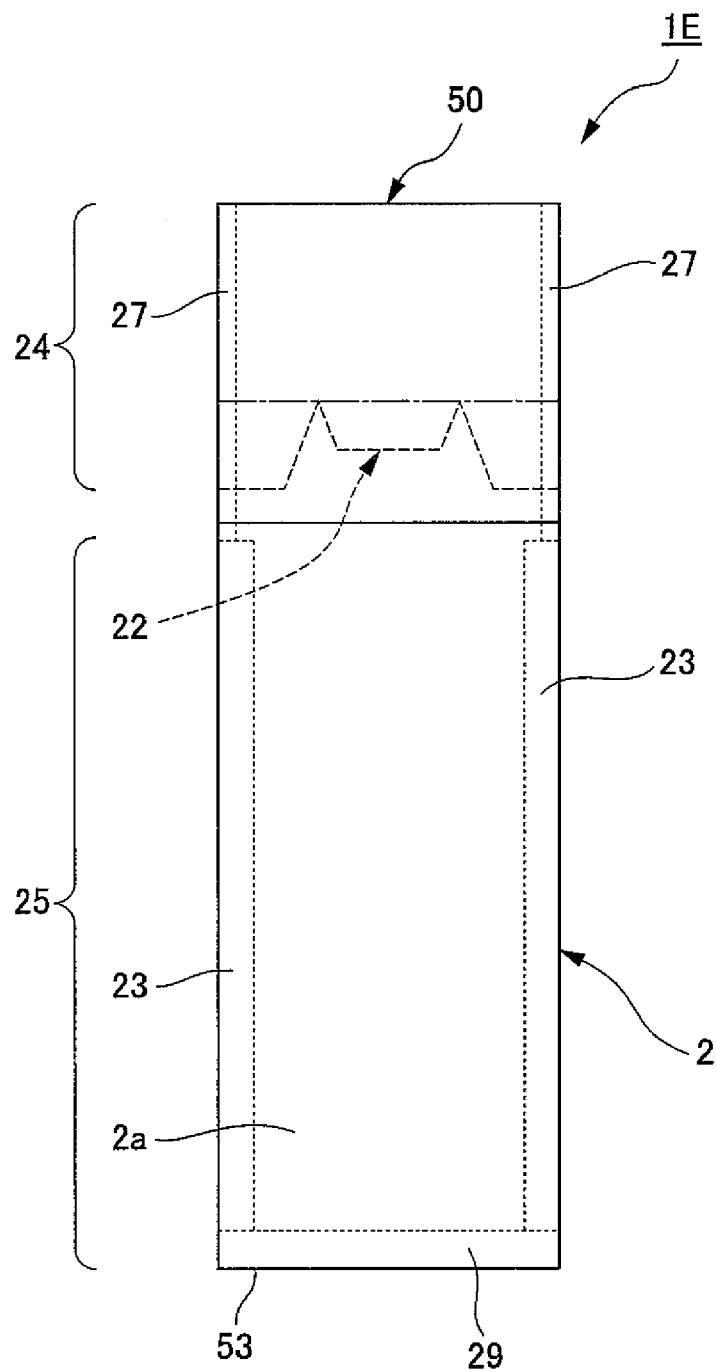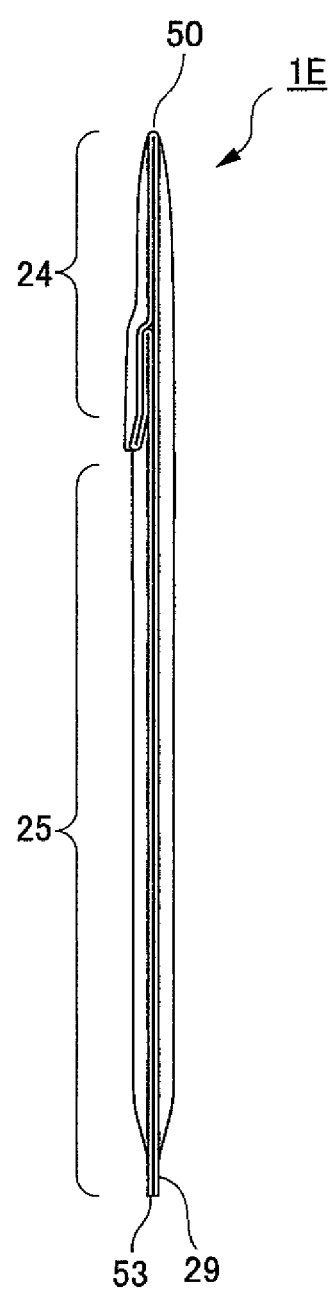

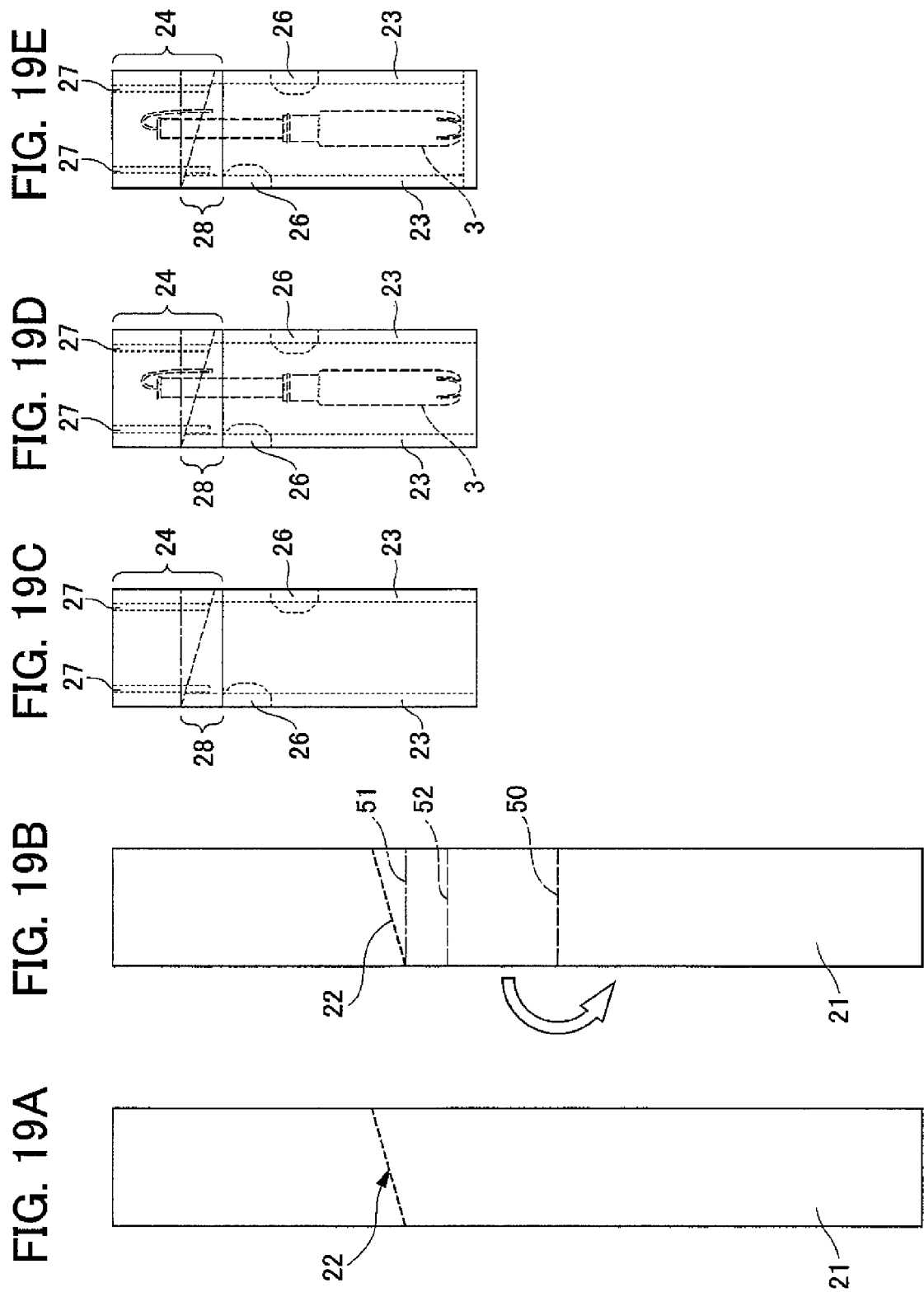

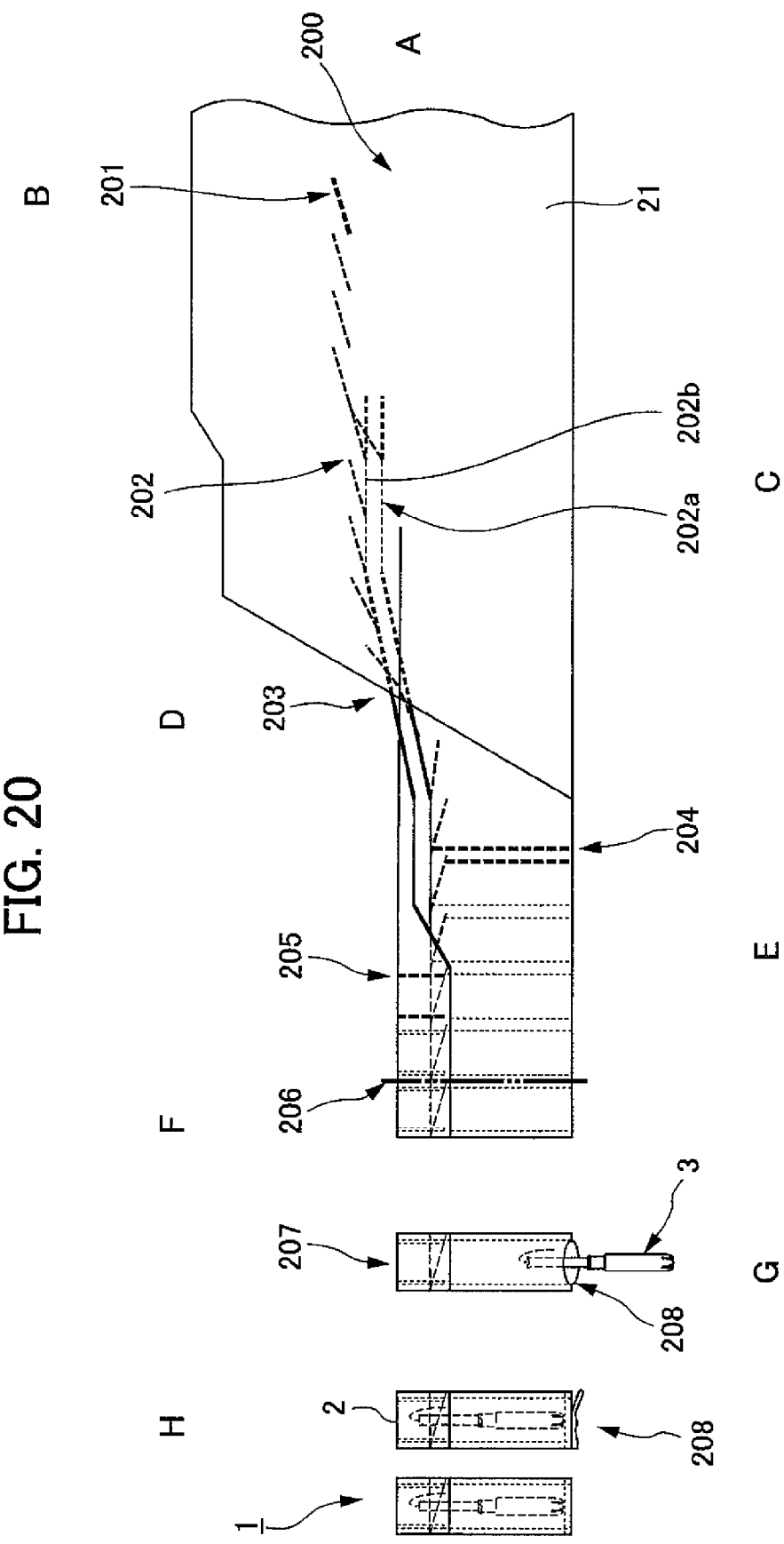

INDIVIDUAL PACKAGE AND METHOD OF MANUFACTURING THE SAME

This application is based on and claims the benefit of priority from Japanese Patent Application No. 2006-114809, filed on Apr. 18, 2006, the content of which is incorporated herein by reference.

BACKGROUND OF THE INVENTION

1. Field of the Invention

The present invention relates to an individual package and a method of manufacturing the same, and particularly, to an individual package for housing a tampon with applicator individually and a method of manufacturing the same.

2. Description of the Related Art

Conventionally, as an absorbent article used as being inserted in a vaginal cavity of a menstruating woman, a so-called sanitary tampon provided with an absorbent body for absorbing a body fluid or the like and a string attached at a rear end of the absorbent body has been widely known. Such a sanitary tampon includes one housing the absorbent body in the internal part of the applicator to insert the absorbent body into a body by means of the applicator, and one inserting the absorbent body into the body not using the applicator but using a finger. For example, according to the sanitary tampon using the applicator, the absorbent body can be inserted into a back of the vaginal cavity more reliably by inserting the applicator with the absorbent body housed therein into a predetermined position of the vaginal cavity and pushing out the absorbent body from the applicator (for example, refer to Japanese Unexamined Patent Application Publication JP-A-No. 2000-279445).

However, the applicator for use in the sanitary tampon disclosed in JP-A 2000-279445 is used by being directly inserted into the body as described above, which involves a problem such that a body fluid such as a menstrual blood adheres to a surface of the applicator after used and the applicator cannot be easily disposed.

Consider a case where a used applicator is disposed of by returning it to an unsealed package bag. In this case, a conventional package bag has a problem that the size of an opening upon unsealing the package bag or the like is not stabilized and the applicator cannot be easily returned to the unsealed package bag. This is because the conventional package bag has a shape that only one side is sealed among the opposite sides of the package bag in a longitudinal direction and the conventional package bag is unsealed by cutting the package bag from a notch-like cut line provided on one end in the longitudinal direction. In addition, it is feared that the package bag is partially separated from the cut line and this becomes an unnecessary waste. Further, in the case of forming the package bag by sealing the sides of the package bag in the longitudinal direction, films easily adhere with each other, which involves a problem such that the clearance cannot be opened well. It can be said that an object of the present invention is to solve these problems.

SUMMARY OF THE INVENTION

The present invention has been made taking the foregoing problems into consideration, and an object of the invention is to provide an individual package which allows a tampon with applicator to be handled easily.

In order to attain the above-described object, the present inventors have found that a clearance having a stable opening shape can be obtained by making the surface of the inside of a flat bag uneven, the sides of the flat bag partially sealed, and by providing a lid portion which is openable and closable in a longitudinal direction on an unsealable portion so as to make the present invention. Specifically, the present invention provides the following individual package and a method of manufacturing the same.

According to the first aspect of the present invention, an individual package including a tampon and a flat bag; the tampon includes: an applicator having an external cylinder and an internal cylinder; and an absorbent body housed so as to be pushed out from the applicator, the tampon being individually enclosed in the flat bag formed with a predetermined sheet member in an elongated shape, the flat bag includes: an unsealable portion formed on one side of the flat bag, so as to enable the tampon to be removed therefrom; and a lid portion provided on one side so as to be openable and closable in a longitudinal direction of the flat bag, the unsealable portion being covered with the lid portion.

According to a first aspect of the present invention, the individual package is provided with a tampon including an applicator having external and internal cylinders and an absorbent body housed so as to be pushed out from the applicator, and a flat bag formed by a predetermined sheet member in an elongated shape. The flat bag is provided with an unsealable portion formed on one side in the flat bag so as to allow the tampon to be removed therefrom, and a lid portion which is openable and closable in a longitudinal direction of the flat bag. The lid portion is disposed so as to cover the unsealable portion. Note that the flat bag includes one which can package at least ⅓ the length of the applicator when it is extended.

In this specification, the word "flat" means plane state, and includes a substantially plane formed of a sheet member having uneven surface. Since the flat bag is formed of a sheet member, the flat bag has a substantially flat surface of the sheet member.

Thus, by providing the unsealable portion formed on one side in the flat bag so as to enable the tampon to be removed therefrom and the lid portion which is openable and closable in a longitudinal direction of the flat bag, a clearance with a stable opening shape can be obtained. Since the lid portion covers the unsealable portion, the lid portion is lifted up on the unsealable portion, so that the position of the unsealable portion can be easily found. For example, in the case of forming the unsealable portion in a mountain shape, the clearance of the unsealable portion is easily widened, which enables the used applicator to be easily put in the unsealable portion. In addition, the unsealable portion can be covered after the used applicator is housed therein by providing the cover portion, which allows the unsealed flat bag to be kept clean. Moreover, for example, the lid portion is bonded to the flat bag by using bonding means capable of rebonding. Consequently, the lid portion can be bonded to the flat bag again even after the unsealing the flat bag so as to allow the unsealed flat bag to be kept clean.

Here, the term "bond", "bonding" includes affix, affixing, and also includes bonding lightly and being capable of re-bonding.

The predetermined sheet member may include, for example, a soft film made of a thermoplastic soft film, but the present invention is not limited thereto. Examples of the predetermined sheet member include a biodegradable film, a nonwoven cloth, a laminate film, and a Japanese paper, which may be used solely or in combination. In the case of using the soft film, for example, when a user carries it and the user unseals it, it is possible to reduce an uncomfortable noise generated by rubbing the films against each other and to improve a touch feeling of the film.

In a second aspect of the individual package as described in a first aspect of the present invention, the lid portion is formed continuously along the unsealable portion, and the unsealable portion is formed in a perforated shape which allows the lid portion to be separated therefrom.

According to the second aspect of the present invention, the unsealable portion is formed continuously along the lid portion in a perforated line which allows the lid portion to be separated therefrom. With this configuration, the unsealable portion is unsealed by the unsealing operation of the lid portion in a longitudinal direction. In addition, the unsealable portion formed in the perforated line is always covered with the lid portion, and the clearance of the unsealable portion is not opened till the perforated line is broken. Accordingly, the tampon enclosed in the flat bag does not directly touch air, so that the tampon can be kept clean.

In a third aspect of the individual package as described in a first or second aspect of the present invention, the lid portion has a graspable portion integrally formed therewith.

According to the third aspect of the present invention, the lid portion has a graspable portion integrally formed therewith. Thereby, the substantially flat bag can be easily unsealed since the unsealing operation is possible by use of the graspable portion. In this case, the term "integrally formed" includes, for example, the case of using a part of the lid portion as the graspable portion. The graspable portion may be formed by folding back the sheet member to form the lid portion. Thus, by forming the graspable portion by folding back the sheet member, the graspable portion is lifted up to be formed in three dimensions, thereby making it possible for a user to more easily know the unsealable portion.

In a fourth aspect of the individual package as described in any one of the first to third aspects of the present invention, the flat bag is applied with unevening process on its inner surface.

According to the fourth aspect of the present invention, the flat bag has a surface of which the inside of a housing portion for housing the tampon with applicator made uneven for example, applied with embossing process. Thereby, a contact area between the sheet members forming the flat bag is reduced and this leads to the advantage that the sheet members hardly stick and easily unstuck. The surface of the sheet member is uneven, which causes a difference in bending resistance of the sheet member. That is, a relatively soft part and a relatively rigid part are generated. Consequently, the soft part receives a force from the rigid part, so that the sheet member is easily bent. As a result, the flat bag can be easily unsealed and a predetermined space can be easily formed when unsealing the bag.

Further, the embossing process may be applied on the surface of the sheet member forming the flat bag. In other words, the unevening process may be applied at least on the inner surface of the flat bag, and it may be applied on the inner surface and the surface of the flat bag. By making the surface of the flat bag uneven, a slip stopper is provided when unsealing.

In a fifth aspect of the individual package as described in any one of the first to fourth aspects of the present invention, the flat bag includes a sealed portion which is formed on the side of the flat bag in the longitudinal direction, so as to project to the inside of the flat bag, the sealed portion being formed by joining one sheet member and another sheet member facing each other.

According to the fifth aspect of the present invention, the flat bag includes a sealed portion which is formed on the side of the flat bag in its longitudinal direction so as to project to the inside of the flat bag, the sealed portion being formed by joining the sheet members facing each other. At least one sealed portion may be formed and a plurality of sealed portions may be formed. In addition, the sealed portions may be formed on the both sides of the flat bag in the longitudinal direction, and the sealed portion may be formed on one side. In this case, the term "inside" includes a direction toward a substantially center axis in a longitudinal direction of the flat bag.

In this manner, by forming the sealed portion on the side of the flat bag, the joined sheet members are integrated and a rigidity of the sealed portion is made higher. For this reason, the sheet members on the sealed portion do not move easily, and a movable range of the sheet members on the sealed portion is made narrower as compared to the width of the clearance of the unsealable portion. Depending on such a difference in the movable range of the sheet members, wide ruck generated when the sheet members are slid is generated on the clearance side, which allows a space to be easily generated on the clearance. Thereby, the applicator after usage of the tampon can be easily put in the flat bag with a space generated on the clearance. Since the sealed portion can be used also as a handle, the sealed portion can be easily treated.

Further, a method of joining the sheet members may include heating, an adhesive, and an ultrasonic, for example. However, the joining method is not limited to them, but any method is applicable as long as the joining portion of sheet members has a peel strength not less than a predetermined intensity and the sheet members can be joined with each other.

In a sixth aspect of the individual package as described in the fifth aspect of the present invention, the sealed portion is formed in a substantially semicircular shape.

According to the sixth aspect of the present invention, the sealed portion is formed so as to project in a substantially semicircular shape in the longitudinal direction of the flat bag. In other words, the shape of the sealed portion has no angular portion. Assume that, for example, in the case of inserting the applicator or the tampon with applicator into the flat bag, the internal cylinder or the external cylinder of the applicator abuts against the sealed portion. Even in this case, it is possible to immediately insert the applicator inside of the flat bag without jamming because the unsealable portion does not have angular portion. In addition, in the case where the sealed portions are formed on the both sides of the flat bag, the applicator or the tampon with applicator can be stabilized because the sealed portions guide the applicator or the tampon with applicator to a substantially center part of the flat bag.

In a seventh aspect of the individual package as described in the fifth or sixth aspects of the present invention, the unsealable portion is formed along a traversing line across a width direction of the flat bag so as to have a predetermined angle with a hypothetical line extending in the longitudinal direction of the flat bag, and the sealed portions are provided on the opposing sides of the flat bag, respectively, and are formed such that a hypothetical line combining the respective sealed portions is parallel with the traversing line.

According to the seventh aspect of the present invention, the unsealable portion is formed so as to have a predetermined angle with a hypothetical line extending in the longitudinal direction of the flat bag. In other words, the unsealed portion is formed in an oblique direction with respect to the hypothetical line extending in the longitudinal direction. Thereby, as compared to the case of forming the unsealable portion so as to be orthogonal to the hypothetical line extending in the longitudinal direction, the clearance of the unsealable portion can be increased. The respective sealed portions are provided so as to be separated from each other such that the inclined angles in a width direction formed by a hypothetical line combining the respective sealed portions make the same angles with the unsealable portion. Consequently, as compared to the case where the respective sealed portions are provided so as to be opposed with each other on opposing sides in the longitudinal direction, it is possible to make a distance between the sealed portions in the width direction longer. That is, it is possible to maintain the internal space of the flat bag on this portion. Accordingly, in the case of providing the respective sealed portions so as to face with each other, there is a narrow portion in the space inside of the flat bag into which the applicator should be inserted. However, in the case of providing the respective sealed portions to be separated from each other in the longitudinal direction, this portion can be made wide as compared to the case of providing the respective sealed portions so as to face with each other. This makes it possible the used applicator to be inserted into the unsealed flat bag more easily. Further, by making the same angles with respect to the unsealable portion, for example, a force is easily transmitted to the unsealable portion upon unsealing the unsealable portion. Note that it is preferable that the sealed portion is located at the position in the range about 15 mm separated from the unsealable portion in the longitudinal direction of the flat bag.

In an eighth aspect of the individual package as described in any one of the first to seventh aspects of the present invention, a length of the flat bag in a width direction is in the range of 180% or more of the maximum diameter of the applicator.

According to the eighth aspect of the present invention, the length of the flat bag in the width direction is made longer than the maximum outer diameter of the external cylinder of the applicator. Specifically, the length of the flat bag in the width direction is formed in the range of 180% to 320% of the maximum outer diameter. With such an arrangement, the length of the substantially flat bag in the width direction is longer than the outline of the applicator. As a consequence, the clearance of the unsealable portion is widened, which allows the used applicator to be easily put into the flat bag. Further, it is difficult for the body fluid or the like adhering to the applicator to adhere to the vicinity of the unsealable portion of the flat bag. Accordingly, it becomes easy to insert the used applicator into the unsealed flat bag, and the applicator can be smoothly discarded without soiling a hand.

In a ninth aspect of the present invention, a manufacturing system for an individual package including a tampon and a flat bag; the tampon includes: an applicator having an external cylinder and an internal cylinder; and an absorbent body housed so as to be pushed out from the applicator, the tampon being individually enclosed in the flat bag formed with a predetermined sheet member in an elongated shape, the manufacturing system comprising means: a sheet supply means for supplying a package sheet in a fixed direction; a perforated line forming means for forming a perforated line at a predetermined position of the package sheet supplied by the sheet supply means; a graspable portion forming means for forming a graspable portion at a predetermined position by folding a part of the package sheet; a folding back means for folding back the package sheet into a predetermined position; a bonding means for bonding at least a part of a width direction of the package sheet folded back by the folding back means at predetermined intervals; a separating means for separating the package sheet bonded by the bonding means at predetermined intervals; a tampon inserting means for inserting a sanitary tampon in the opening; and an opening joining means for joining the opening.

According to the ninth aspect of the present invention, the manufacturing system for an individual package includes: sheet supply means for supplying a package sheet in a fixed direction; perforated line forming means for forming a perforated line at a predetermined position of the package sheet supplied by the sheet supply means; graspable portion forming means for forming a graspable portion at a predetermined position by folding a part of the package sheet; folding back means for folding back the package sheet at a predetermined position; bonding means for bonding at least a part of a width direction of the package sheet folded back by the folding back means at predetermined intervals; separating means for separating the package sheet bonded by the bonding means at predetermined intervals; tampon inserting means for inserting a sanitary tampon in an opening; and opening joining means for joining the opening. With this configuration, it is possible to provide a manufacturing system for an individual package by which the used applicator can be easily inserted into the unsealed flat bag so as to enable the applicator to be smoothly processed without soiling a hand.

In a tenth aspect of the manufacturing system as described in the ninth aspect of the present invention, the bonding means includes the sealed portion forming means for forming a sealed portion formed in a predetermined shape.

According to the tenth aspect of the present invention, the manufacturing system for an individual package is further provided with sealed portion forming means for forming a sealed portion formed in a predetermined shape as the bonding means. With this configuration, it is possible to provide a manufacturing system for an individual package by which the used applicator can be easily inserted into the unsealed flat bag so as to enable the applicator to be smoothly processed without soiling a hand.

According to an eleventh aspect of the present invention a method of manufacturing an individual package including a tampon and a flat bag; the tampon includes: an applicator having an external cylinder and an internal cylinder; and an absorbent body housed so as to be pushed out from the applicator, the tampon being individually enclosed in the flat bag formed by a sheet member in an elongated shape, the method comprising steps of: a sheet supply step of supplying a package sheet in a fixed direction; a perforated line forming step of forming a perforated line at a predetermined position of the package sheet supplied by the sheet supply step; a graspable portion forming step of forming a graspable portion at a predetermined position by folding a part of the package sheet; a lid portion forming step of forming a lid portion by folding back the package sheet at a predetermined position; a joining step of joining the package sheet folded back by the lid portion forming step; a sealed portion forming step of forming a sealed portion formed into a predetermined shape; a tampon inserting step of inserting a sanitary tampon into the opening; and an opening joining step of joining the opening.

According to the eleventh aspect of the present invention, the method of manufacturing an individual package includes: a sheet supply step of supplying a package sheet in a fixed direction; a perforated line forming step of forming a perforated line at a predetermined position of the package sheet supplied by the sheet providing step; a graspable portion forming step of forming a graspable portion at a predetermined position by folding a part of the package sheet; a lid portion forming step of forming a lid portion by folding back the package sheet at a predetermined position; a joining step of joining the package sheet folded back by the lid portion folding step; a sealed portion forming step of forming a sealed portion formed in a predetermined shape; a tampon inserting step for inserting a sanitary tampon in an opening; and an opening joining step for joining the opening. With this configuration, it is possible to provide a method of manufacturing an individual package by which the used applicator can be easily inserted in the unsealed flat bag so as to enable the applicator to be smoothly processed without soiling a hand.

According to the present invention, it is possible to provide an individual package which allows a tampon with applicator to be easily treated.

BRIEF DESCRIPTION OF THE DRAWINGS

FIGS. 6A and 6B are front views of the individual package, each showing a positional relation of a sealed portion;

FIG. 14A is a front view of an individual package according to a fourth embodiment of the invention;

FIG. 14B is a side view of an individual package according to a fourth embodiment of the invention;

FIG. 16A is a front view of an individual package according to a fifth embodiment of the invention;

FIG. 16B is a side view of an individual package according to a fifth embodiment of the invention;

FIG. 17A is a front view of an individual package according to a sixth embodiment of the invention;

FIG. 17B is a side view of an individual package according to a sixth embodiment of the invention;

FIGS. 19A to 19E are schematic views each showing a method of manufacturing an individual package;

FIG. 20 is a schematic view showing a state that an individual package is manufactured;

DETAILED DESCRIPTION OF THE INVENTION

Hereinafter, embodiments of the present invention will be described with reference to the drawings. The embodiments of the present invention are not limited to the following examples, and a technical range of the invention is not limited thereto.

Figure 1:
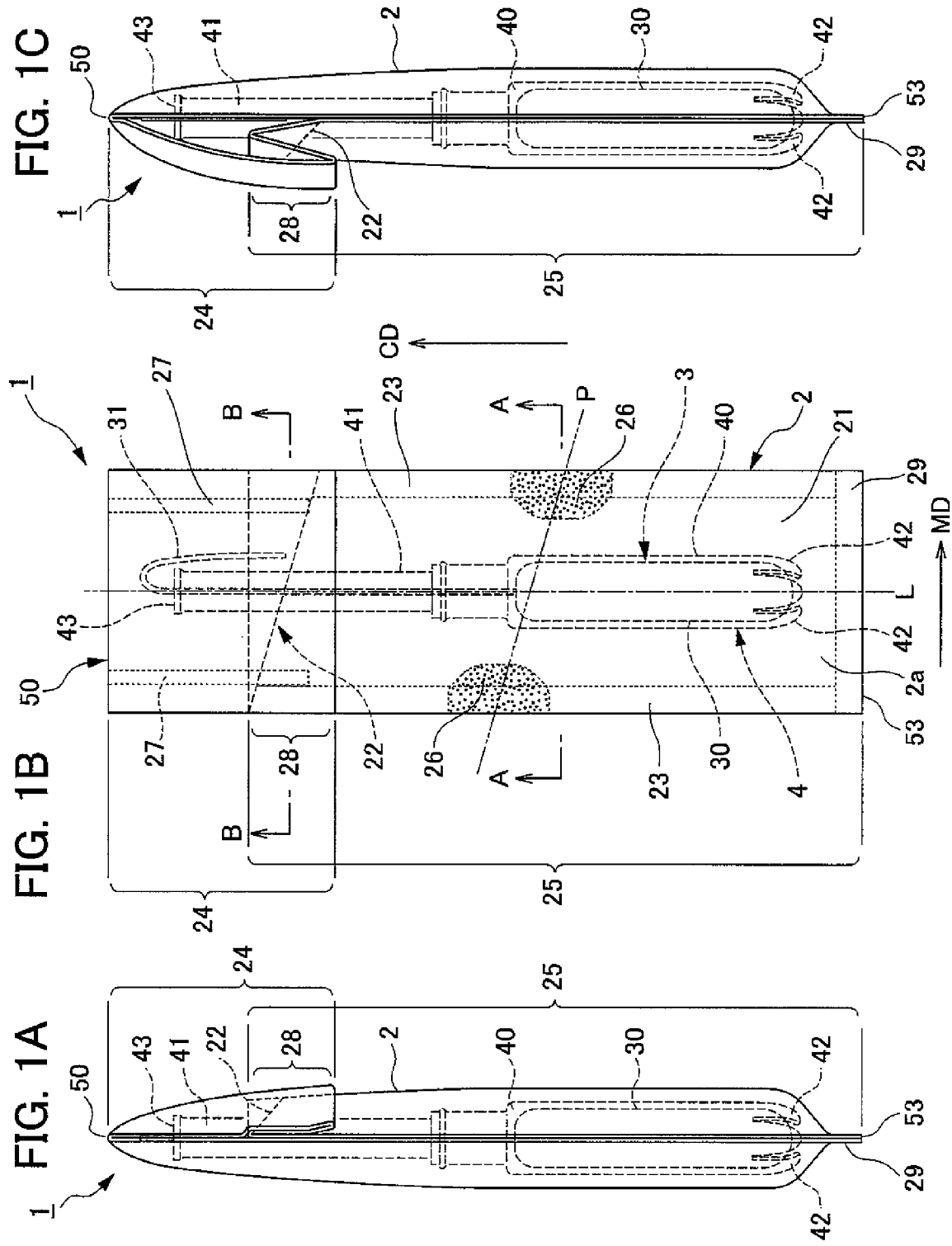
FIG. 1A is a left side view of an individual package according to a first embodiment of the invention.
FIG. 1B is a front view of an individual package according to a first embodiment of the invention.
FIG. 1C is a right side view of an individual package according to a first embodiment of the invention.
Figure 2:
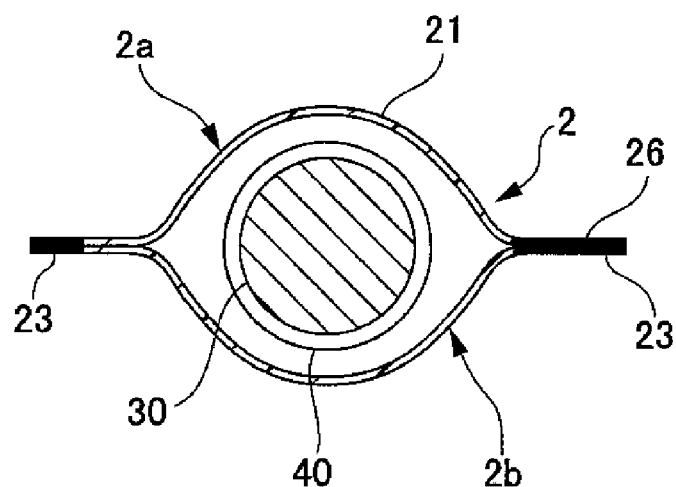
FIG. 2 is a cross sectional view of the individual package in FIG. 1B taken along the line A-A.
Figure 3:
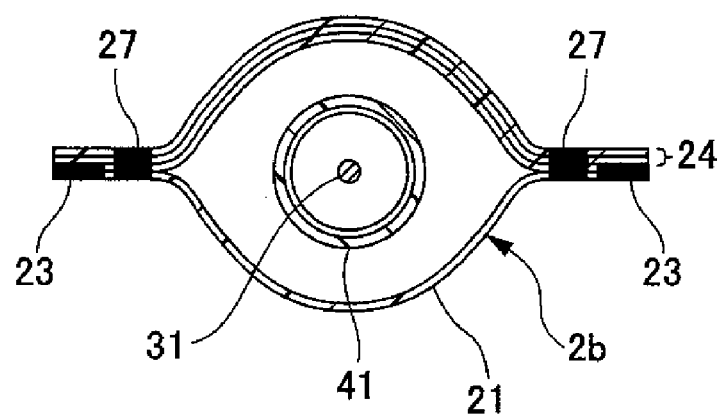
FIG. 3 is a cross sectional view of the individual package in FIG. 1B taken along the line B-B.
Figure 4:
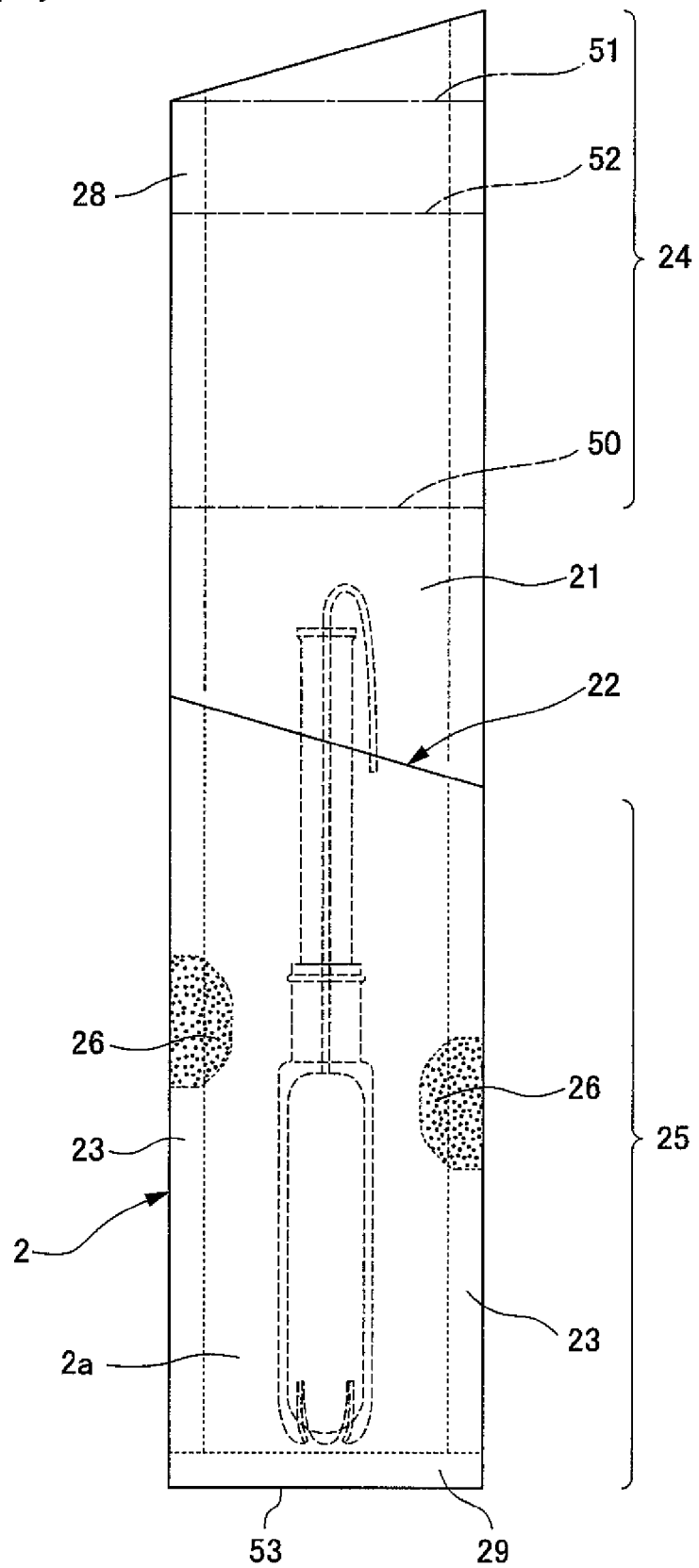
FIG. 4 is a front view showing an unsealed state of the individual package in FIG. 1B.
Figure 5:
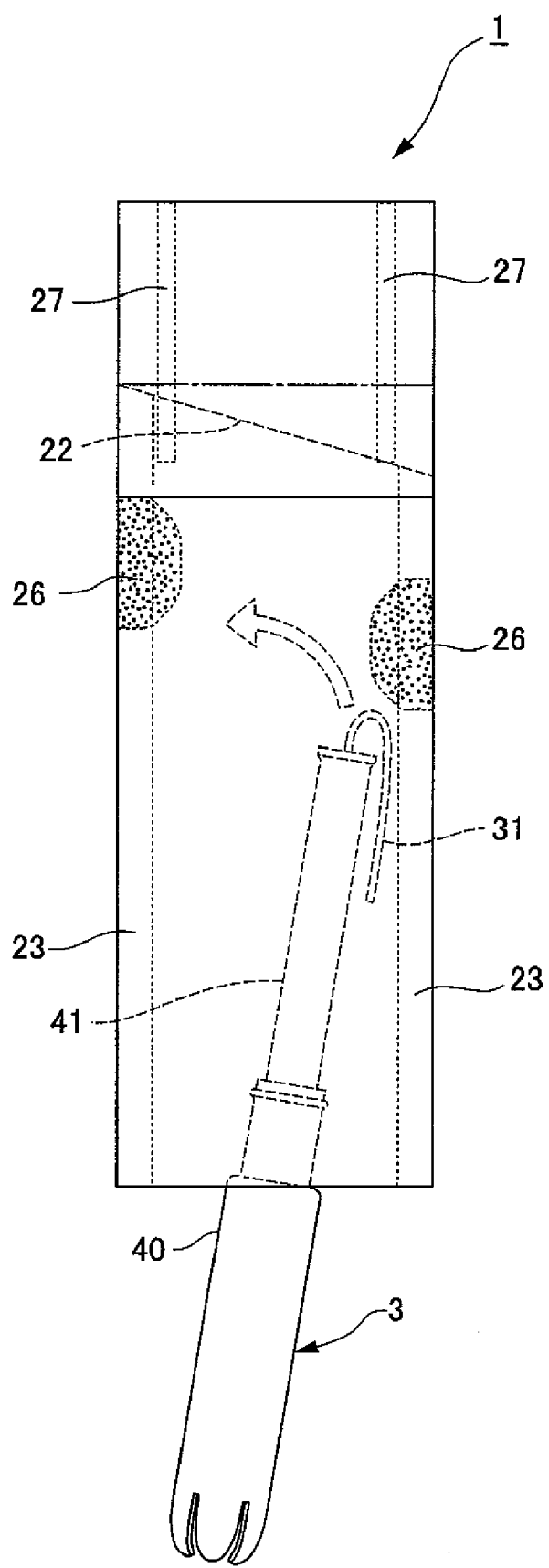
FIG. 5 is a front view of the individual package according to the first embodiment, showing a relation between a sealed portion at the sides of the flat bag in the longitudinal direction and insertion of a tampon.
Figure 7A:
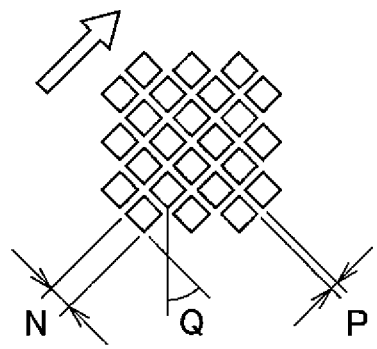
FIGS. 7A and 7B are schematic views each showing an embossed pattern.
Figure 7B:
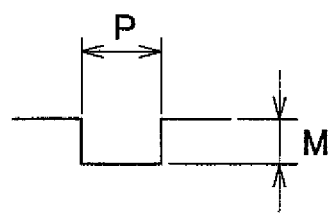
Figure 8:
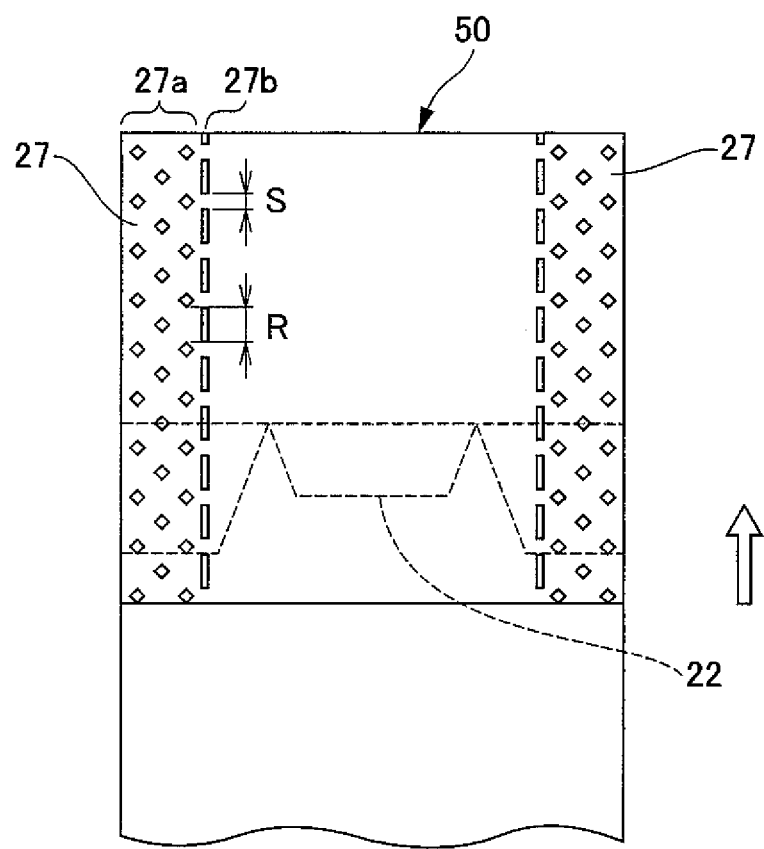
FIG. 8 is a schematic view of a lid portion for explaining the embossed pattern.
Figure 9:
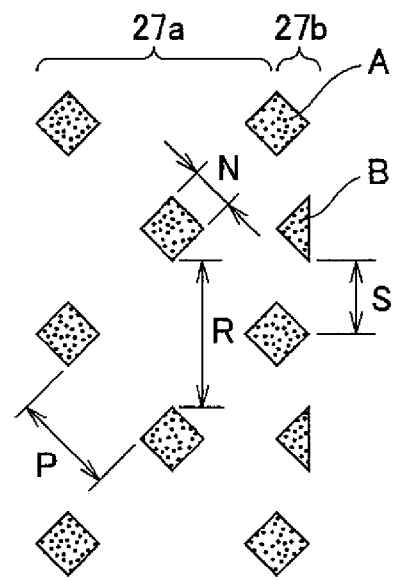
FIG. 9 is a schematic view showing the embossed pattern.
Figure 10:
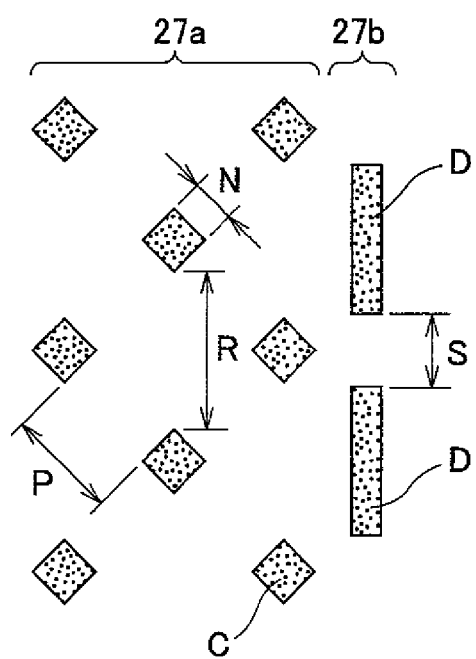
FIG. 10 is a schematic view showing the embossed pattern.

FIG. 1A is a left side view of an individual package according to a first embodiment of the invention. FIG. 1B is a front view of an individual package according to a first embodiment of the invention. FIG. 1C is a right side view of an individual package according to a first embodiment of the invention. For the purpose of explanation, a lid portion has partially opened. FIG. 2 is a cross sectional view of the individual package in FIG. 1B taken along the line A-A. FIG. 3 is a cross sectional view of the individual package in FIG. 1B taken along the line B-B. FIG. 4 is a front view showing an unsealed state of the individual package in FIG. 1A to C. FIG. 5 is a front view of the individual package according to the first embodiment, showing a relation between a sealed portion at the sides of the flat bag in the longitudinal direction and insertion of a tampon. FIGS. 6A and 6B are front views of the individual package, each showing a positional relation of a sealed portion. FIGS. 7A and 7B are schematic views each showing an embossed pattern. FIG. 8 is a schematic view of a lid portion for explaining the embossed pattern. FIG. 9 is a schematic view showing the embossed pattern. FIG. 10 is a schematic view showing the embossed pattern.

Figure 11A:
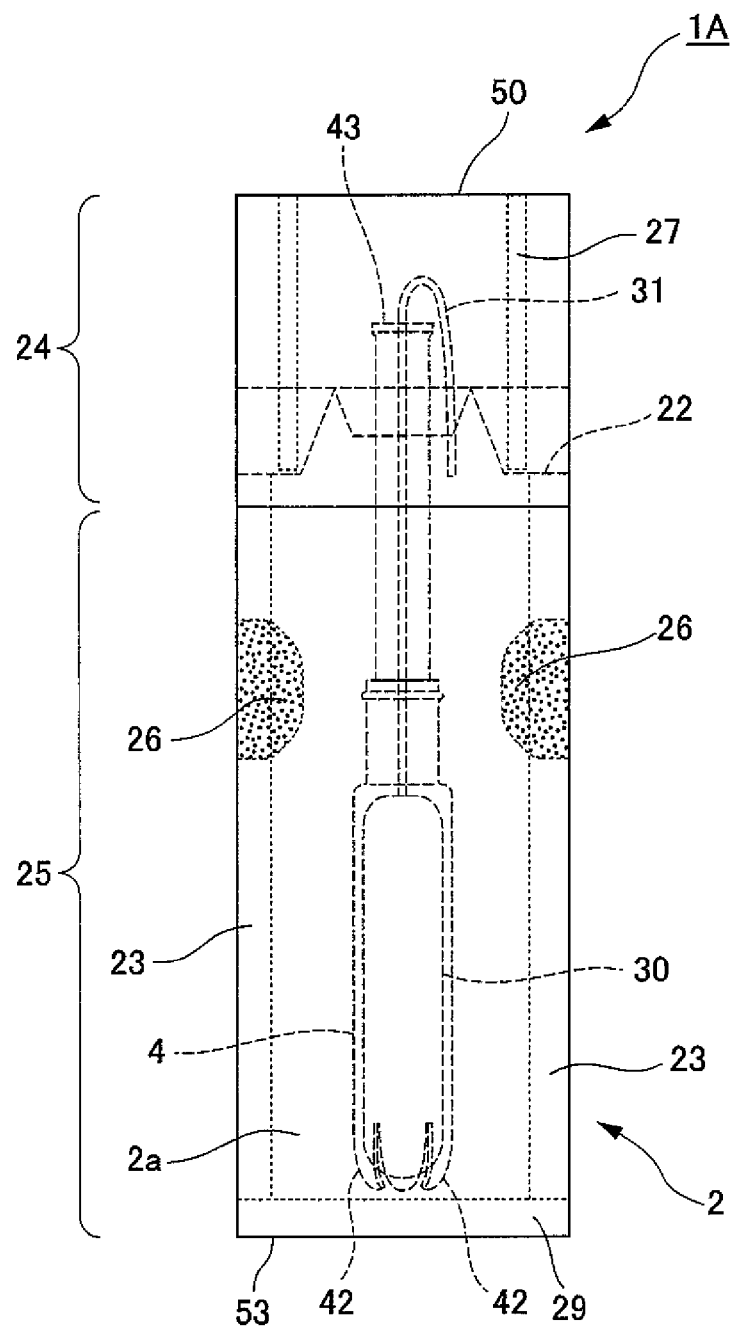
FIG. 11A is a front view of an individual package according to a second embodiment of the invention.
Figure 11B:
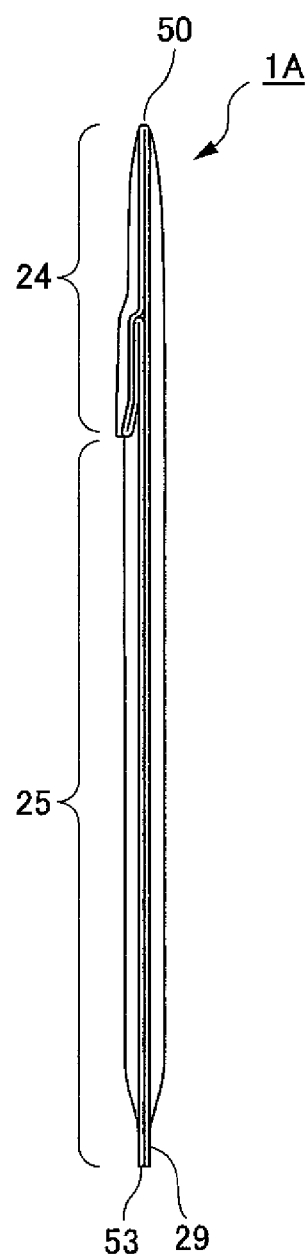
FIG. 11B is a side view of an individual package according to a second embodiment of the invention.
Figure 12:
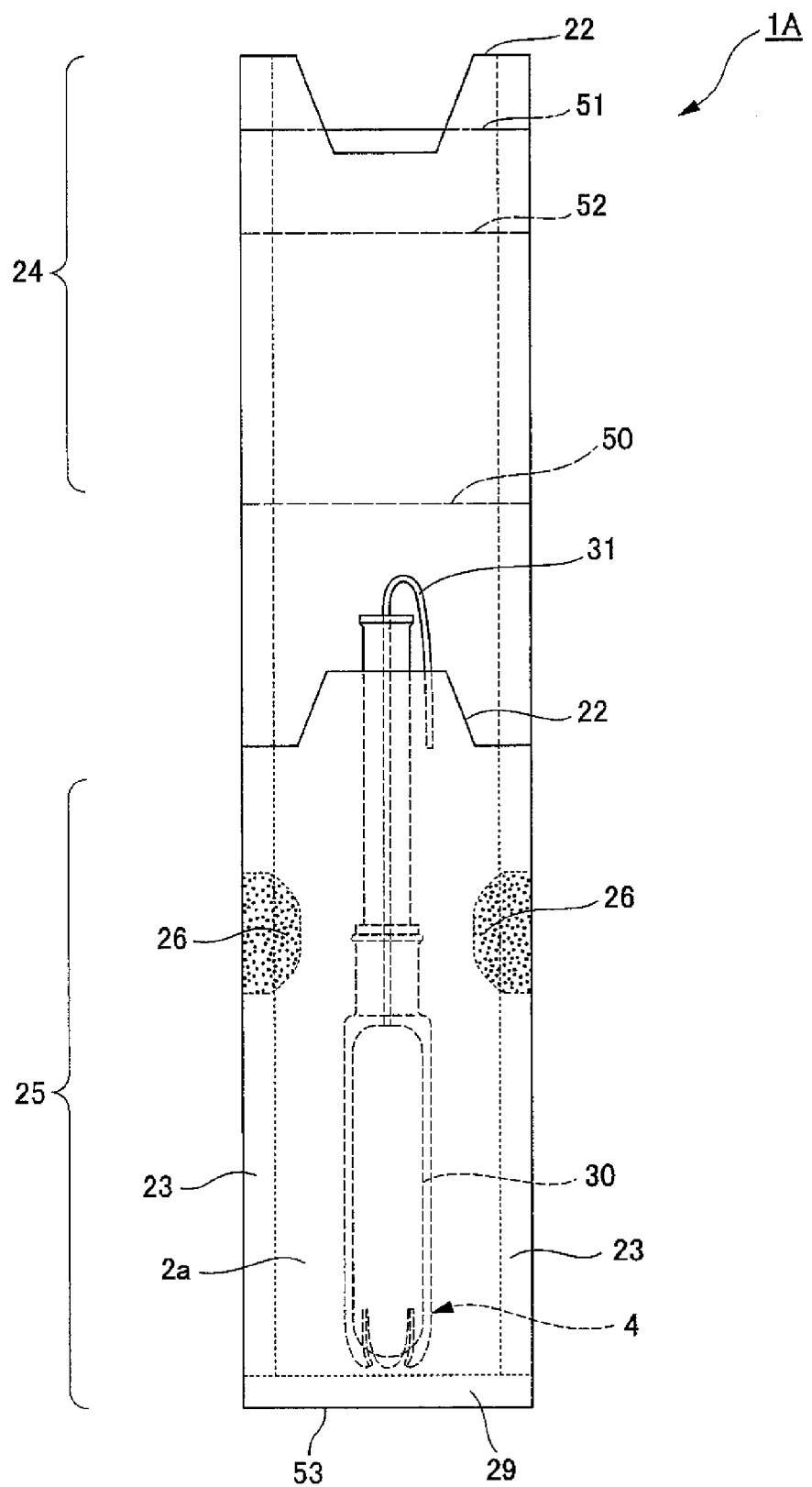
FIG. 12 is a front view showing an unsealed state of the individual package in FIG. 11A.
Figure 13:
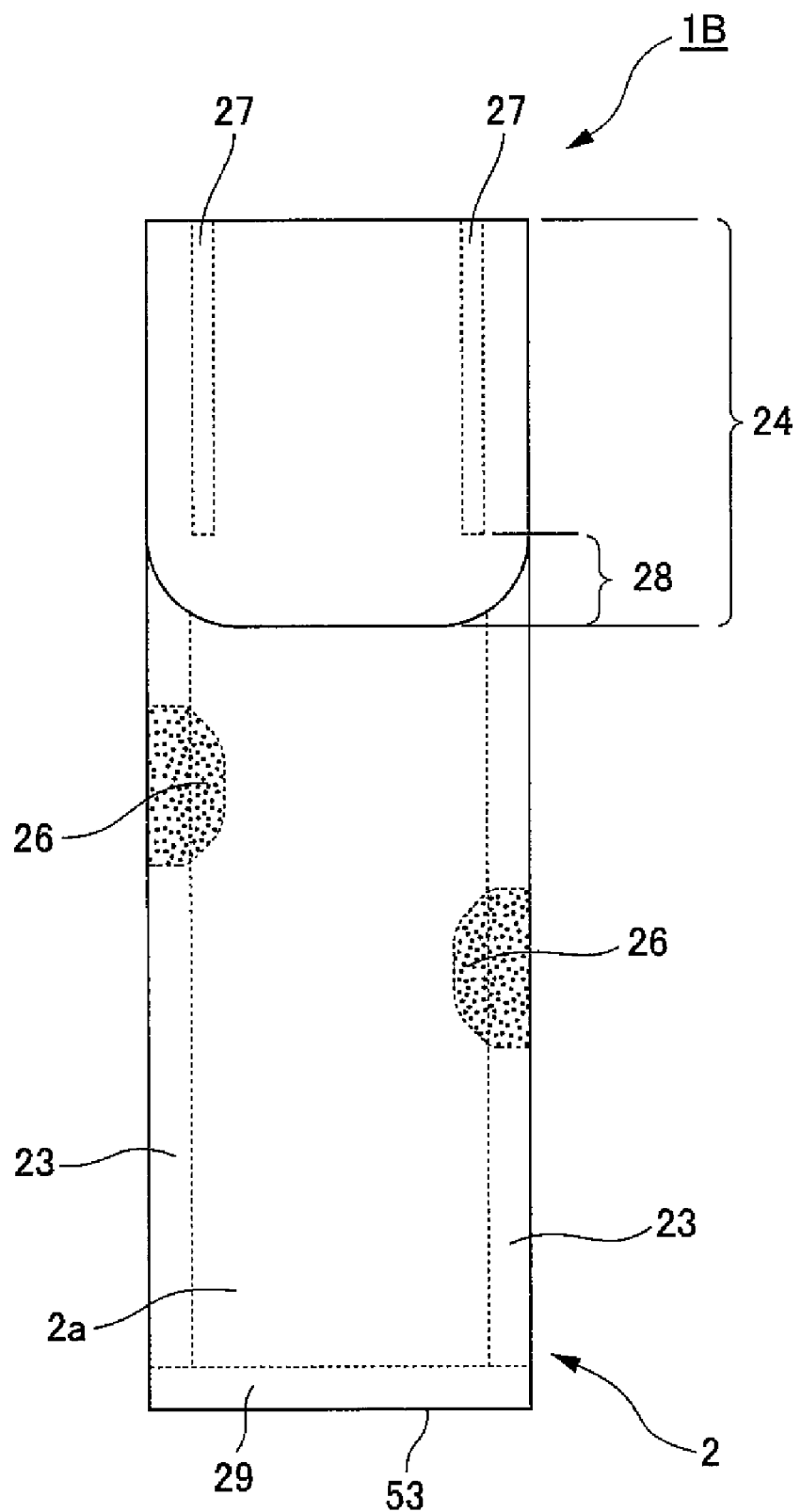
FIG. 13 is a front view of an individual package according to a third embodiment of the invention.
Figure 15:
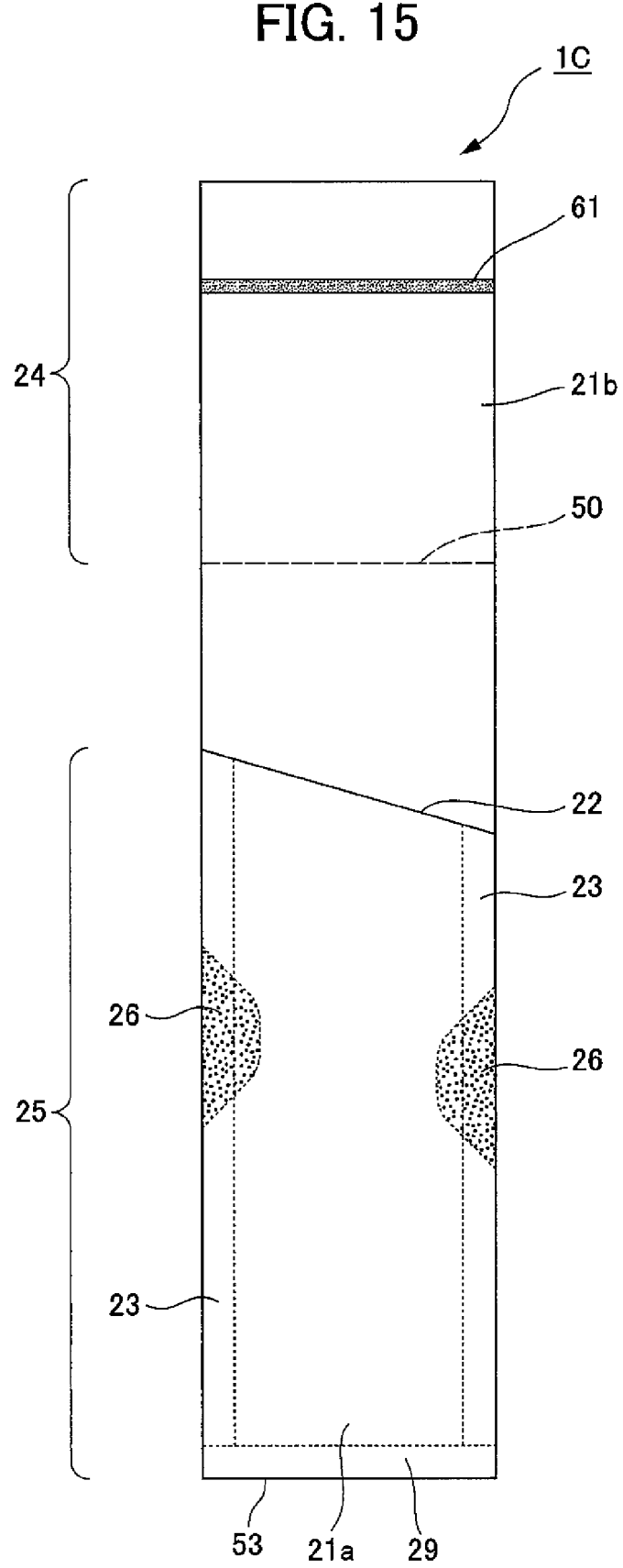
FIG. 15 is a front view showing an unsealed state of the individual package in FIG. 14A.
Figure 21:
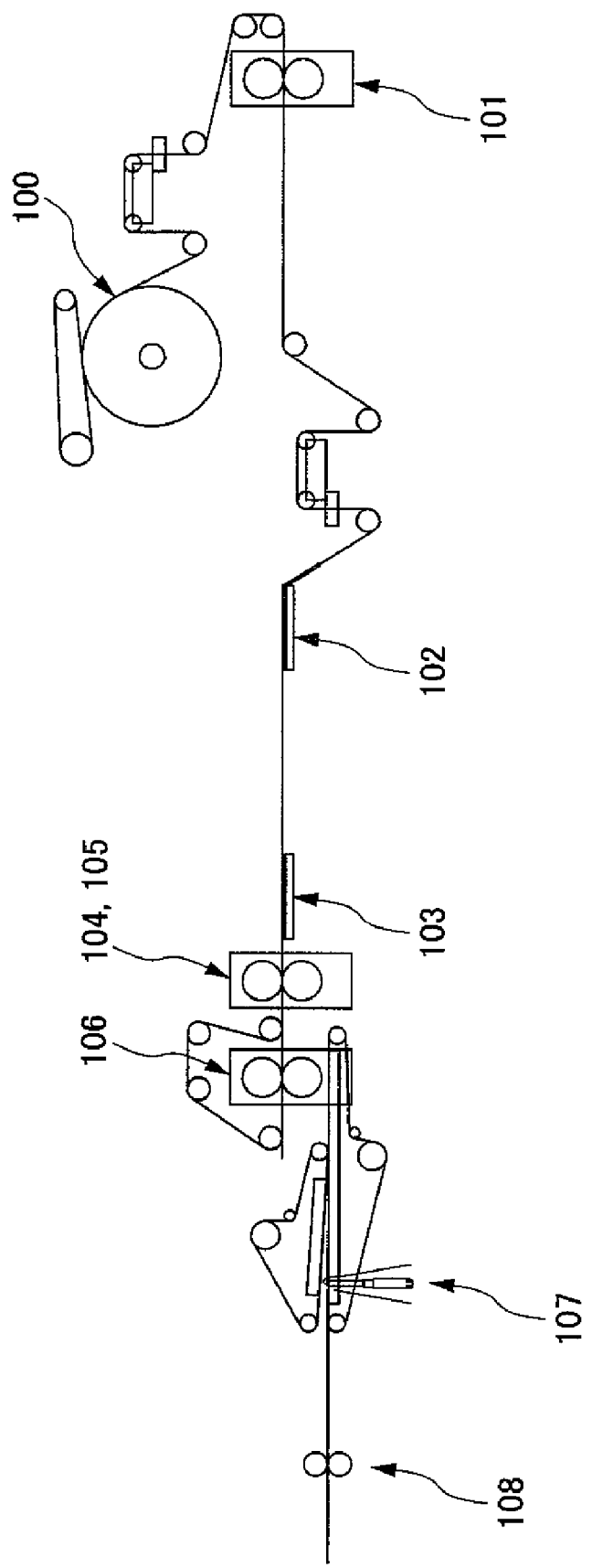
FIG. 21 is a schematic view showing a manufacturing system for an individual package.
Figure 22:
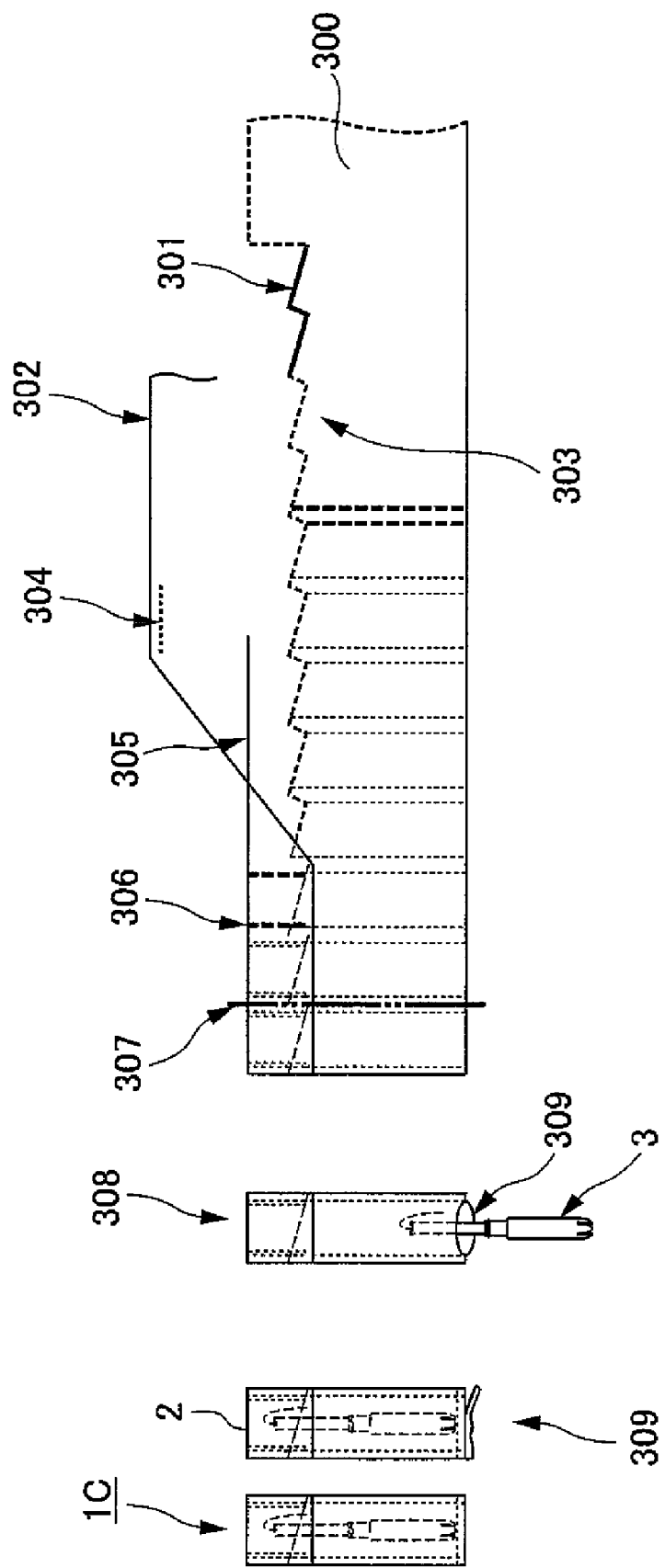
FIG. 22 is a schematic view showing a state that the individual package according to the fourth embodiment is manufactured.

FIG. 11A is a front view of an individual package according to a second embodiment of the invention. FIG. 11B is a side view of an individual package according to a second embodiment of the invention. In FIG. 11B, for the purpose of simplification of the explanation, the applicator is not shown. FIG. 12 is a front view showing an unsealed state of the individual package in FIGS. 11A and 11B. FIG. 13 is a front view of an individual package according to a third embodiment of the invention. FIG. 14A is a front view of an individual package according to a fourth embodiment of the invention. FIG. 14B is a side view of an individual package according to a fourth embodiment of the invention. In FIG. 14B, for the purpose of simplification of the explanation, the applicator is not shown. FIG. 15 is a front view showing an unsealed state of the individual package in FIGS. 14A and 14B. FIG. 16A is a front view of an individual package according to a fifth embodiment of the invention. FIG. 16B is a side view of an individual package shown in FIG. 16A. FIG. 17A is a front view of an individual package according to a sixth embodiment of the invention. FIG. 17B is a side view of an individual package shown in FIG. 17A. FIGS. 18A to 18D are views for explaining a test state of peel strength. FIGS. 19A to 19E are schematic views each showing a method of manufacturing an individual package. FIG. 20 is a schematic view showing a state that an individual package is manufactured. FIG. 21 is a schematic view showing a manufacturing system for an individual package. FIG. 22 is a schematic view showing a state that the individual package according to the fourth embodiment is manufactured.

First Embodiment

1. Entire Constitution

As shown in FIGS. 1A to 4, an individual package 1 includes a tampon with applicator 3 including an applicator 4 having an external cylinder 40 and an internal cylinder 41 and a flat package bag 2 formed in a substantially vertically long shape, the package bag 2 being formed from a package sheet 21 which is a sheet member. The package bag 2 has a housing portion 25, and the tampon with applicator 3 is housed in the housing portion 25. The package bag 2 has also an unsealable portion 22 formed in a perforated shape and a lid portion 24 formed continuously along the unsealable portion 22 so as to cover the unsealable portion 22. The lid portion 24 includes a graspable portion 28 integrally formed with the lid portion 24. Sealed portions 26 are formed on the sides of the housing portion 25 in a longitudinal direction. The sealed portion 26 is formed in a substantially semicircular shape so as to project to the inside. The sealed portion 26 bonds package sheets 21 facing each other. While the sealed portion 26 is provided in the first embodiment, the invention is not limited thereto, and the constitution without the sealed portion 26 can be also used.

2. Individual Package a. Entire Length

The length of the individual package 1 in the longitudinal direction is preferably a length obtained by adding 10 mm to 40 mm to the entire length of the applicator 4, for example. Specifically, defining a long type and a compact type which is convenient to carry, the followings can be exemplified. According to the long type, in a light type (manufactured by Uni-Charm Corporation) that the entire length of the applicator 4 is 145 mm, the longitudinal length of the individual package 1 is in the range of 155 mm to 185 mm; in a regular type (manufactured by Uni-Charm Corporation) that the entire length of the applicator 4 is 116.5 mm, the longitudinal length of the individual package 1 is in the range of 127 mm to 157 mm; in a super type (manufactured by Uni-Charm Corporation) that the entire length of the applicator 4 is 119.5 mm, the longitudinal length of the individual package 1 is in the range of 130 mm to 160 mm; and in other products having the entire length of the applicator 4 of 126 mm, the longitudinal length of the individual package 1 is in the range of 136 mm to 166 mm.

In addition, according to the compact type, in a regular type (manufactured by Uni-Charm Corporation) that the entire length of the applicator 4 is 85 mm, the longitudinal length of the individual package 1 is in the range of 95 mm to 125 mm, and in a super type (manufactured by Uni-Charm Corporation) that the entire length of the applicator 4 is 88 mm, the longitudinal length of the individual package 1 is in the range of 98 mm to 128 mm.

b. Length of Housing Portion

The length of the housing portion of the individual package 1 may be, for example, not less than the length of the external cylinder and not more than the length obtained by adding 10 mm to the entire length of the applicator 4. Specifically, defining a long type and a compact type, the followings can be exemplified. According to the long type, in a light type (manufactured by Uni-Charm Corporation) that the length of the external cylinder 40 is 101 mm and the entire length of the applicator 4 is 145 mm, the length of the housing portion is in the range of 101 mm to 155 mm; in a regular type (manufactured by Uni-Charm Corporation) that the length of the external cylinder 40 is 68.5 mm and the entire length of the applicator 4 is 116.5 mm, the length of the housing portion is in the range of 68.5 mm to 126.5 mm; in a super type (manufactured by Uni-Charm Corporation) that the length of the external cylinder 40 is 71.2 mm and the entire length of the applicator 4 is 119.5 mm, the length of the housing portion is in the range of 71.2 mm to 129.5 mm; and in other products that the length of the external cylinder 40 is 71.8 mm and the entire length of the applicator 4 is 126 mm, the length of the housing portion is in the range of 71.8 mm to 136 mm.

In addition, according to the compact type, in a regular type (manufactured by Uni-Charm Corporation) that the length of the external cylinder 40 is 63.5 mm and the entire length of the applicator 4 is 85 mm, the length of the housing portion is in the range of 63.5 mm to 95 mm, and in a super type (manufactured by Uni-Charm Corporation) that the length of the external cylinder 40 is 64 mm and the entire length of the applicator 4 is 88 mm, the length of the housing portion is in the range of 64 mm to 98 mm.

c. Width

The length of the individual package 1 in the width direction is preferably in the range of 180% to 320% of the outer diameter of the external cylinder 40 of the applicator 4, for example, and more preferably, it is about 270% of the outer diameter of the external cylinder 40 of the applicator 4.

Specifically, defining a long type and a compact type, the followings can be exemplified. According to the long type, in a light type (manufactured by Uni-Charm Corporation) that the external diameter of the external cylinder 40 is 12.9 mm, the widthwise length of the individual package 1 is in the range of 23 mm to 41 mm, and preferably, 29 mm. In a regular type (manufactured by Uni-Charm Corporation) that the external diameter of the external cylinder 40 is 13.4 mm, the widthwise length of the individual package 1 is in the range of 24 mm to 43 mm, and preferably, 30 mm. In a super type (manufactured by Uni-Charm Corporation) that the external diameter of the external cylinder 40 is 16.4 mm, the widthwise length of the individual package 1 is in the range of 30 mm to 52 mm, and preferably, 36 mm. In other products having the external diameter of the external cylinder 40 of 17.6 mm, the widthwise length of the individual package 1 is in the range of 23 mm to 56 mm, and preferably, 39 mm.

In addition, according to the compact type, in a regular type (manufactured by Uni-Charm Corporation) that the external diameter of the external cylinder 40 is 13.4 mm, the widthwise length of the individual package 1 is in the range of 24 mm to 43 mm, and preferably, 30 mm; and in a super type (manufactured by Uni-Charm Corporation) that the external diameter of the external cylinder 40 is 16 mm, the widthwise length is in the range of 29 mm to 51 mm, and preferably, 36 mm.

d. Width of Bonded Sides

The width of the bonded sides on opposing sides in the longitudinal direction of the individual package 1 is, for example, 3 mm to 6 mm.

e. Lid Portion

The length of the lid portion 24 in the longitudinal direction is, for example, a length obtained by subtracting the length of the housing portion from the entire length of the individual package 1. Specifically, followings can be exemplified. According to the long type, in a light type (manufactured by Uni-Charm Corporation) that the entire length of the individual package 1 is in the range of 155 mm to 185 mm, the longitudinal length of the lid portion 24 is in the range of 20 mm to 104 mm; in a regular type (manufactured by Uni-Charm Corporation) that the entire length of the individual package 1 is in the range of 127 mm to 157 mm, the longitudinal length of the lid portion 24 is in the range of 20 mm to 107 mm; in a super type (manufactured by Uni-Charm Corporation) that the entire length of the individual package 1 is in the range of 130 mm to 160 mm, the longitudinal length of the lid portion 24 is in the range of 20 mm to 109 mm; and in other products that the entire length of the individual package 1 is in the range of 136 mm to 166 mm, the longitudinal length of the lid portion 24 is in the range of 80 mm to 115 mm.

In addition, according to the compact type, in a regular type (manufactured by Uni-Charm Corporation) that the entire length of the individual package 1 is in the range of 95 mm to 115 mm, the longitudinal length of the lid portion 24 is in the range of 20 mm to 81.5 mm, and in a super type (manufactured by Uni-Charm Corporation) that the entire length of the individual package 1 is in the range of 98 mm to 118 mm, the longitudinal length of the lid portion 24 is in the range of 20 mm to 84 mm.

f. Graspable Portion

The longitudinal length of the graspable portion 28 in the lid portion 24 is, for example, in the range of 5 mm to 20 mm.

3. Tampon with Applicator

The tampon with applicator 3 includes an absorbent body 30, a string 31 extended from the rear end of the absorbent body 30, and the applicator 4 for housing the absorbent body 30 and the string 31 therein. For example, the absorbent body 30 may be formed by compressing a hydrophilic fiber such as cotton and rayon to cover the surface with a liquid permeation sheet such as a nonwoven cloth. The absorbent body 30 may absorb the body fluid such as a menstrual blood to swell when the absorbent body 30 is inserted in the vaginal cavity of a menstruating woman. While the absorbent body 30 is inserted in the vaginal cavity of the menstruating woman, the string 31 is kept out of the vaginal cavity, and then, the used absorbent body 30 can be removed from the vaginal cavity by pulling this string 31.

The applicator 4 is made of a synthetic resin material, and has the external cylinder 40 having the absorbent body 30 housed therein and the internal cylinder 41 which is slidably inserted in the external cylinder 40 as being opposed to the rear end of the absorbent body 30. On the front end of the external cylinder 40, a plurality of petals 42 are divided each other to be integrally formed. The string 31 extended from the rear end of the absorbent body 30 is inserted in the internal cylinder 41 to project backward from a rear end 43 of the internal cylinder 41. In the case of using the tampon with applicator 3, the external cylinder 40 of the applicator 4 is inserted into the vaginal cavity to push the internal cylinder 41 into the inside of the external cylinder 40. In this time, the absorbent body 30 contained in the external cylinder 40 is pushed out by the internal cylinder 41, the pedals 42 on the front end of the external cylinder 40 are modified to be opened, so that the absorbent body 30 is inserted into the vaginal cavity.

4. Package Bag

The package bag 2 is formed to be substantially flat having one surface 2a which is one side and the other surface 2b which is the other side by folding the package sheet 21 at a folding-back portion 50. The one and other surfaces 2a and 2b facing each other are joined with each other at bonded sides 23 on opposing sides in the longitudinal direction. The one and other surfaces 2a and 2b are joined with each other also at a bottom bonded portion 29 which is an end opposed to the folding-back portion 50. The one surface 2a of the package bag 2 is provided with the lid portion 24 in the vicinity of the folding-back portion 50 formed by being folded back from the other surface 2b. The lid portion 24 is provided with the graspable portion 28 which is formed by folding back a part of the lid portion 24 to the inside, namely, to the side of the one surface 2a. In addition, one surface 2a has the unsealable portion 22. The unsealable portion 22, the lid portion 24, and the graspable portion 28 are integrally formed to be continued on the package sheet 21. The unsealable portion 22 is formed as being covered with the lid portion 24.

The unsealable portion 22 is formed in a perforated shape, and the unsealable portion 22 can be separated from the lid portion 24 on the perforated line. That is, the lid portion 24 can be opened and closed in the longitudinal direction by breaking the perforated line of the unsealable portion 22. The perforated line can be formed by using, for example, a laser apparatus ($CO_2$ LASER MARKER ML-G930, manufactured by Keyence Corporation). According to the first embodiment, the unsealable portion 22 is formed by a straight perforated line extending and traversing in the width direction of the package bag 2, but the invention is not limited thereto. The unsealable portion 22 may be in a semicircular, wave-like, or mountain shape. Further, the unsealable portion 22 may be formed in a direction orthogonal to the longitudinal direction. Preferably, the unsealable portion 22 is formed in an oblique direction having a predetermined angle with respect to the hypothetical line L extending in the longitudinal direction. When the unsealable portion 22 is formed in the oblique direction, the clearance of the unsealable portion 22 is increased to allow the used applicator 4 to be easily inserted in the unsealable portion 22. Further, the unsealable portion 22 may not be formed by the perforated line, and it may have a shape which can be cut off as a predetermined line.

The lid portion 24 has the graspable portion 28. The graspable portion 28 is formed by folding back the lid portion 24 to the side of the one surface 2a. Specifically, the graspable portion 28 is formed by mountain-folding a mountain-folded portion 52 of the lid portion 24 to the inside of the package sheet 21 and folding back a valley-folded portion 51 to the side of the other surface 2b. Although, according to the first embodiment, the graspable portion 28 is formed in a substantially rectangle, the invention is not limited thereto, and the graspable portion 28 may be formed in a substantially semicircular shape.

On the opposite sides of the lid portion 24 in the longitudinal direction, lid portion bonding portions 27 for bonding the lid portion 24 and the other surface 2b are provided. The lid portion bonding portions 27 may be arranged on the opposite side ends of the lid portion 24 in the longitudinal direction. In addition, the lid portion bonding portions 27 may be bonded including at least a part of the graspable portion 28. The bottom bonded portion 29 to join the one surface 2a with the other surface 2b is formed on the lower end opposed to the lid portion 24 of the package bag 2 in the longitudinal direction. The bonded sides 23 obtained by joining the package sheets 21 of the one and other surfaces 2a and 2b are formed on the opposite edges of the housing portion 25 in the longitudinal direction.

The sealed portion 26 formed in a substantially semicircular shape is arranged on the bonded sides 23. The sealed portion 26 is formed by joining portions of the package sheets 21 of the one and other surfaces 2a and 2b so as to project toward a center axis in the longitudinal direction of the package bag 2. The sealed portions 26 are formed in a substantially semicircular shape, and each sealed portion 26 is formed so as to project to the inside of the package bag 2. According to the first embodiment, the sealed portion 26 is formed in a substantially semicircular shape. However, the invention is not limited thereto, and the shape subjected to the process for chamfering the corner is available. Specifically, for example, a chamfered trapezoid may be available. Assume that, as shown in FIG. 5, upon insertion of the tampon with applicator 3 in a manufacturing step, the tampon with applicator 3 may abut against the sealed portion 26. Even in this case, it is possible to immediately insert the applicator inside of the package bag 2 without jamming because the process for chamfering corners is applied.

Even when the used applicator 4 is inserted from the unsealable portion, and even when the external cylinder 40 of the applicator 4 abuts against the sealed portion 26, it is possible to insert the applicator 4 inside of the package bag 2 without jamming. Further, the tampon with applicator 3 can be stabilized on the substantially center part of the package bag 2. When, in this case, respective sealed portions 26 are provided so as to be separated from each other in the longitudinal direction, a width of the housing portion 25 can be made wide (refer to FIGS. 6A and 6B).

The individual package 1 is formed by the package sheet 21 and is provided with the embossing process in its inside. Examples of the package sheet 21 include a film made of high-density polyethylene (HUPE), low-density polyethylene (LDPE), linear low-density polyethylene (LLDPE), and a combination of these materials. Preferably, the above-described materials with a weight in the range of 20 g/m$^2$ to 35 g/m$^2$ can be used. In addition, these materials may be made into a single layer or may be a plurality of layers. The package sheet is not limited to the above-described materials, and further examples of the package sheet include a thermoplastic resin such as polypropylene (PP), EVA resin (EVA), PET resin (PET), and polyvinyl chloride resin (PVC), a biodegradable film, a nonwoven cloth, a laminate film, and a Japanese paper, which may be used solely or in combination.

The package sheet 21 may be formed with a mold release process such as corona process and silicon process is applied on the partial or entire inner surfaces of the films facing each other when the package sheet 21 is made into a package bag state. This is because, due to these processes, a friction coefficient of the package sheet is lowered to makes it difficult for the package sheets to stick with each other.

It is preferable that a surface roughness of the package sheet 21 has a MMD value indicating variation of the friction coefficient in the range of 0.03 to 0.06 (a KES surface roughness test) This is because a contact area of the package sheets 21 is large, the friction is hardly generated, and the surface is not slippery if the MMD value is too low. If the MMD value is too high, on the other hand, concavities and convexities of the facing inner surfaces are engaged with each other and the surface is not slippery.

Preferably, a bending rigidity of the package sheet 21 has a value B indicating a bending rigidity value per 1 cm$^2$ in the range of $0.005 \times 10^{-4}$ Nm/m to $0.040 \times 10^{-4}$ Nm/m (a KES bending rigidity test).

As for the package sheet 21, embossing process is applied on the inner surfaces of the films facing each other when the package sheet 21 is made into a package bag state. An available example of the embossing process in one in which an emboss roll is used, an embossing temperature is in the range of a room temperature to 4° C., and circle patterns are zigzag-aligned, a height of a pattern after molding a film is 90 μm. In addition, in the embossing process, the thickness of the package sheet after the embossing process is preferably in the range of 0.07 mm to 0.13 mm.

Here, heat sealing process for processing an embossed pattern in the bonded sides 23, the lid portion bonding portion 27, and the bottom bonded portion 29 of the package bag 2 will be described below. In the heat sealing process, for example, a seal temperature is in the rang of 80° C. to 110° C. and a pressure is in the range of 15 kgf/cm$^2$ to 30 kgf/cm$^2$.

Examples of the embossed pattern of the heat seal are shown in FIGS. 7A and 7B. For the bonded sides 23, an embossed pattern having a groove depth M of 1.0 mm; an opening N of 0.8×0.8 mm; a pitch P of 1.5 mm; an inclined angle Q of 45°; and a hound's-tooth shape is used, for example. For the lid portion bonding portion 27, an embossed pattern having a groove depth M of 1.0 mm; an opening N of 0.6×0.6 mm; a pitch P of 1.5 mm; an inclined angle Q of 45°; and a hound's-tooth shape is used, for example. For the bottom bonded portion 29, an embossed pattern having a groove depth M of 1.0 mm; an opening N of 0.8×0.8 mm; a pitch P of 1.2 mm; an inclined angle Q of 45°; and a hound's-tooth shape is used, for example. Further, for the lid portion affixed portion 27, an embossed pattern having a groove depth M of 1.0 mm; an opening N of 0.3×1.2 mm; a pitch P of 1.0 mm; an inclined angle Q of 45°; and a hound's-tooth shape is used, for example. Thus, by making the shape of the emboss into a rectangle, the lid portion 24 can be easily peeled off.

When the temperature of the heat sealing process is high, the package sheets 21 may be hardly peeled off each other due to melting. As a result, as shown in FIG. 8, by setting pitches R and S having different patterns on the substantially center part 27a and the inner end 27b of the lid portion bonding portion 27, for example, the lid portion bonding portion 27 is easily broken from a boundary line between the rectangular emboss and a no-emboss, which allows the lid portion 24 to be easily peeled off. Forming the lid portion 24 so as to be easily peeled off allows the lid portion 24 to be easily unsealed in a longitudinal direction.

Specifically, an embossed pattern as shown in FIG. 9 can be exemplified. FIG. 9 has, on a substantially center part 27a, a pattern A with a groove depth M of 1.0 mm (refer to FIG. 7B); an opening N of 0.6×0.6 mm; a pitch P of 1.4 mm; an inclined angle Q of 45° (refer to FIG. 7A); and a hound's-tooth shape. FIG. 9 has a pattern B, which is an approximately triangle with a pitch S of 1 mm and one side of 0.6 mm, on the inner end 27b. Thus, the pitch S on the inner end 27b is 1 mm while the pitch R of the center part 27a is 2 mm, whereby the pitch on the inner end 27b becomes narrow and the lid portion 24 can be easily unsealed in the longitudinal direction.

As shown in FIG. 10, for the inner end 27b, a pattern D is used which is a rectangle of 1.0×2.0 mm extended in the longitudinal direction with a pitch S of 1 mm on the inner end 27b, in addition to the pattern A on the center portion 27a. Thereby, the pitch S on the inner end 27b is 1 mm while the pitch R of the center part 27a is 2 mm, whereby the pitch on the inner end 27b becomes narrow and the lid portion 24 can be easily unsealed in the longitudinal direction.

Second Embodiment

An individual package 1A according to a second embodiment of the invention is similar to the individual package 1 of the first embodiment. The individual package 1A of the second embodiment will be described below focusing on a different point from the individual package 1 of the first embodiment.

As shown in FIGS. 11A and 12, in the individual package 1A according to the second embodiment, the unsealable portion 22 is formed in a mountain shape. In other words, the perforated line is formed in a mountain shape. Specifically, mountain shapes are formed on the substantially center part of the unsealable portion 22 to be formed on the side of the lid portion 24 and the side of the housing portion 25, respectively. On the other hand, a part of the unsealable portion 22 to be formed on the side of the housing portion 25 is folded back on the valley-folded portion 51. The respective mountain shapes are formed by the perforated line to be connected to each other. Thus, formation of the perforated line of the unsealable portion 22 into a mountain shape allows the clearance to be easily opened. This enables the used applicator to be easily returned.

According to the second embodiment, the sealed portions 26 are provided facing each other. Thus, provision of the sealed portions 26 facing each other makes it possible to hold the tampon with applicator 3 on the substantially center part stably. For example, provision of respective sealed portions 26 substantially in parallel with the opening allows the opening of a stable shape to be easily formed.

Third Embodiment

An individual package 1B according to a third embodiment of the invention is similar to the individual package 1 of the first embodiment. The individual package 1B of the third embodiment will be described below focusing on a different point from the individual package 1 of the first embodiment.

As shown in FIG. 13, in the individual package 1B of the third embodiment, the graspable portion 28 to be arranged on the lid portion 24 is formed in a substantially semicircular shape. In this manner, the graspable portion 28 to be arranged on the lid portion 24 may be not only a rectangle but also a chamfered substantially semicircular shape etc.

Fourth Embodiment

An individual package 1C according to a fourth embodiment of the invention is similar to the individual package 1 of the first embodiment. The individual package 1C of the fourth embodiment will be described below focusing on a different point from the individual package 1 of the first embodiment.

As shown in FIGS. 14A, 14B and 15, the individual package 1C of the fourth embodiment is formed with package sheets 21a and 21b to form one and other surfaces are provided separately. That is, a flat bag is formed by allowing the package sheet 21a configuring one surface and the package sheet 21b configuring the other surface to face with each other and joining the opposing sides thereof in the longitudinal direction. The lid portion 24 is formed with the individual package 1C folded back on the folding-back portion 50. On the end of the lid portion 24 in the longitudinal direction, the graspable portion 28 is arranged. The opposing sides of the lid portion 24 in the longitudinal direction are joined by a part of the package sheet 21a, the package sheet 21b, and the lid portion bonding portions 27 formed in the longitudinal direction. In addition, the end in the vicinity of the clearance of the lid portion 24 is bonded, for example, by hot melting in a lid portion bonding portion 61 formed in a width direction.

Fifth Embodiment

An individual package 1D according to a fifth embodiment of the invention is similar to the individual package 1 of the first embodiment. The individual package 1D of the fifth embodiment will be described below focusing on a different point from the individual package 1 of the first embodiment.

As shown in FIG. 16A, in the individual package 1D of the fifth embodiment, the unsealable portion 22 is formed in a mountain shape. In other words, the perforated line is formed in a mountain shape. Specifically, mountain shapes are formed on the substantially center part of the unsealable portion 22 to be formed on the side of the lid portion 24 and the side of the housing portion 25, respectively. On the other hand, a part of the unsealable portion 22 to be formed on the side of the housing portion 25 is folded back on the valley-folded portion 51. The respective mountain shapes are joined by the perforated line. The individual package 1D of the fifth embodiment may have, for example, an entire length of 145 mm, a width of 45 mm, a longitudinal length of the lid portion 24 of 60 mm, and a length of the housing portion of 98 mm. In addition, the graspable portion 28 may be 13 mm in length, and the width of the bonded sides and the width of the bottom bonded portion each may be 5 mm, for example.

According to the individual package 1D of the fifth embodiment, the embossing process can be applied on the lid portion 24 and the bonded sides 23 at once. Specifically, defining each bonding width of the bonded sides 23 and the lid portion bonding portions 27 to be 5 mm, the embossing process can be applied on the opposing sides in the longitudinal direction, respectively. In this case, the lid portion bonding portions 27 and the bonded sides 23 may be subjected to embossing processes of different patterns. In this case, it is preferable to select a pattern such that the peal intensity of the lid portion bonding portion 27 is lower than that of the bonded sides 23. Thus, by forming the perforated line of the unsealable portion 22 into a mountain shape, the clearance is easily opened and the embossing process at once is available, so that molding of the individual package 1D becomes easy.

Sixth Embodiment

An individual package 1E according to a sixth embodiment of the invention is similar to the individual package 1D of the fifth embodiment. The individual package 1E of the sixth embodiment will be described below focusing on a different point from the individual package 1D of the fifth embodiment.

As shown in FIG. 17A, the individual package 1E of the sixth embodiment may be constituted such that the width of the bonded sides is different from the lid portion bonding width. For example, the lid portion bonding width is made narrower than the width of the bonded sides, whereby it is possible to reduce the embossed area and to unseal the lid portion 24 easily. In this case, the lid portion bonding portions 27 and the bonded sides 23 may be subjected to embossing processes of different patterns, or they may use the same embossed pattern.

Hereinafter, with reference to Examples, an optimum material for the package sheet will be examined.

Example 1

Using an embossed polyethylene film (PE) with a weight of 23 g/m$^2$, a surface roughness and a bending rigidity were tested.

Surface Roughness Test
KES test: Used device, KES FB-4S manufactured by Kato Tech Corporation
Sample: Length 100 mm, Width 100 mm Calculation Method: $MMD$ value (surface roughness)= ($MD$ directional $MMD$ value+$CD$ directional $MMD$ value)/2

Bending Rigidity Test
KES test: Used device, KES FB-2 manufactured by Kato Tech Corporation
Sample: Length 100 mm, Width 100 mm Calculation Method: Value $B$ (bending rigidity)=$MD$ directional value $B$ ($10^{-4}$ Nm/m)

MD direction: Width direction, CD direction: Longitudinal direction

TABLE 1

|  |  | Comparative Example 1 | Example 1 | Example 2 | Example 3 | Comparative Example 2 |
|---|---|---|---|---|---|---|
| Film Property | weight (g/m$^2$) | 23 | 23 | 30 | 35 | 30 |
|  | Resin | PE | PE | PE | PE | PP |
|  | Embossed/Non-embossed | Non-embossed | Embossed | Embossed | Embossed | Non-embossed |
| KES test | Surface Roughness MMD | 0.008 | 0.041 | 0.035 | 0.025 | 0.009 |
|  | Bending Rigidity Value B | 0.006 | 0.009 | 0.017 | 0.024 | 0.055 |
| Sensory Evaluation | Unsealability | bad | good | excellent | good | bad |
|  | Volume of Sound | good | good | good | good | bad |
|  | Softness | excellent | excellent | good | good | bad |

Example 2

Using an embossed polyethylene film (PE) with a weight of 30 g/m$^2$, a test was carried out under the same conditions as the first embodiment.

Example 3

Using an embossed polyethylene film (PE) with a weight of 35 g/m$^2$, a test was carried out under the same conditions as first embodiment.

Comparative Example 1

Using a non-embossed polyethylene film (PE) with a weight of 23 g/m$^2$, a test was carried out under the same conditions as the first embodiment.

Comparative Example 2

Using a non-embossed polypropylene film (PP) with a weight of 30 g/m$^2$, a test was carried out under the same conditions as the first embodiment.
Evaluation
a. Unsealability
Excellent: very easily unsealed
Good: easily unsealed
Bad: hardly unsealed
b. Volume of Sound
Good: Sound is not loud
Bad: Sound is loud
c. Softness
Excellent: very soft
Good: soft
Bad: hard As being obvious from the above-described results, the package sheet having no embossing process applied as Comparative Example 1 is evaluated to be hardly unsealed from the sensory evaluation, which indicates that the package sheet is not suitable for the sheet used for the individual package 1. As Comparative Example 2, the package sheet having no embossing process applied and using a polypropylene film (PP) is evaluated to be hardly unsealed, to generate a loud sound, and also to be hard from the sensory test, which indicates that the package sheet is not suitable for the sheet used for the individual package 1 as same as Comparative Example 1.

Figure 18A:
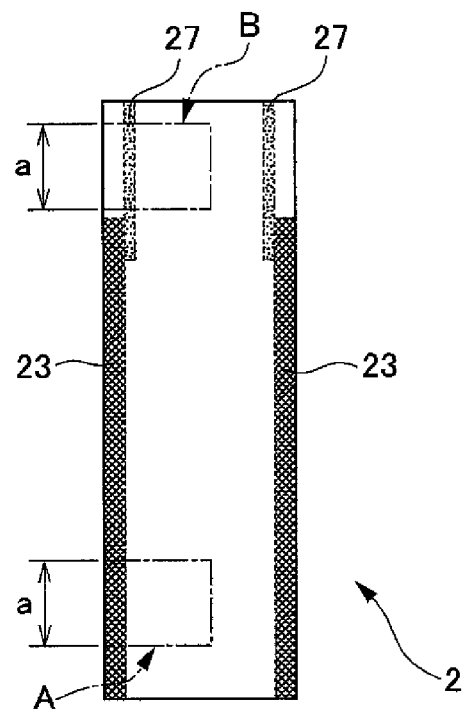
FIGS. 18A to 18D are views for explaining a test state of peel strength.
Figure 18B:
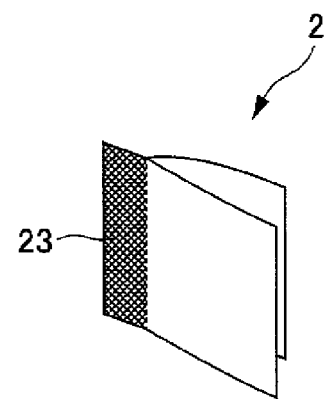
Figure 18C:
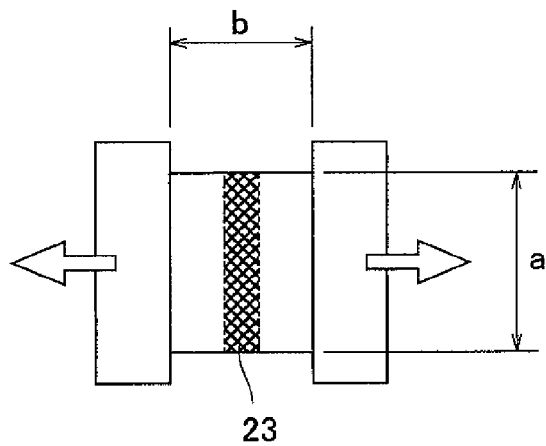
Figure 18D:
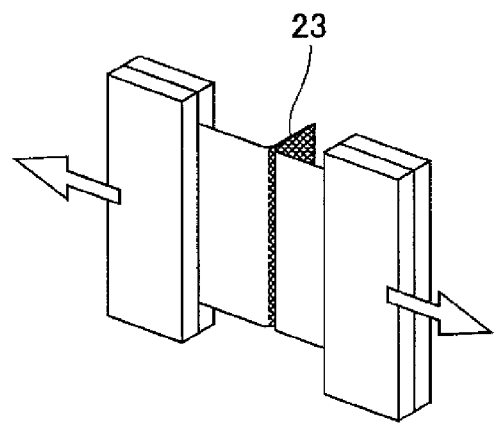

Next, the peel strengths of the bonded sides 23 and the lid portion bonding portion 27 will be examined. As shown in FIG. 18B, a test was carried out such that a portion A and a portion B in the package bag 2 were cut off to clip the opposing ends in a chuck of Autograph (FIGS. 18C and 18D).

Example 4

Under the condition that an embossing temperature was in the range of 99° C. to 106° C. and an embossing pressure was in the range of 20 kgf/cm$^2$, the peel strength was tested using an embossed polyethylene film (PE) with a weight of 30 g/m$^2$.

TABLE 2

|  | g/m$^2$ | Bonded Sides | Lid portion bonding portion |
|---|---|---|---|
| Maximum test force | N/25 mm | 2.2 | 1.2 |
| Depth of groove | mm | 1.0 mm | 1.0 mm |
| Opening | mm | 0.8 mm | 0.6 mm |
| Pitch | mm | 1.5 mm | 1.5 mm |
| Arrangement | Degree | 45 degrees | 45 degrees |

Used Device
Autograph AG-1 manufactured by Shimadzu System Solutions Co., Ltd.
Evaluation Sample
A test was carried out about the portion A (the bonded sides 23) and the portion B (the bonded sides 23) in FIG. 18A by using a test chip (length a: 25 mm).
Embossed Pattern
For the bonded sides, an embossed pattern having a groove depth of 1.0 mm, an opening of 0.8×0.8 mm, a pitch of 1.5 mm, and an arrangement of 45° was used.
For the lid portion bonding portion, an embossed pattern having a groove depth of 1.0 mm, an opening of 0.6×0.6 mm, a pitch of 1.5 mm, and an arrangement of 45° was used.
Evaluation Method
A test was carried out under the condition that a space between the chucks was 20 mm and a peel rate was 100 mm/min.
Evaluation
From above-described matters, it is found that the bonded sides 23 have relatively high peel strength (the maximum test force). It is also found that, since the lid portion bonding portion 27 has a relatively low peel strength (the maximum test force), the lid portion 24 is easily peeled off.
Manufacturing Method
Next, a method of manufacturing method of an individual package 1 according to the present invention will be described. According to the method of the invention, the individual package 1 is manufactured in which a tampon with applicator 3 provided with an applicator 4 having an external cylinder 40 and an internal cylinder 41 and an absorbent body 30 housed so as to be pushed out from the applicator 4 is individually enclosed in an elongated long package bag 2 which is formed by a predetermined package sheet 21. As shown in FIG. 19A to 19E, the manufacturing method includes a sheet supply step of supplying a package sheet in a fixed direction; a perforated line forming step of forming a perforated line at a predetermined position of the package sheet 21 supplied by the sheet supply step; a graspable portion forming step of forming a graspable portion 28 at a predetermined position by folding down a part of the package sheet 21; a lid portion forming step of forming a lid portion 24 by folding back the package sheet 21 at a predetermined position; a joining step for joining the package sheet 21 folded down by the lid portion forming step; a sealed portion forming step of forming a sealed portion 26 formed into a predetermined shape; a tampon inserting step of inserting the tampon with applicator 3 into an opening; and an opening joining step of joining the opening.

An object to be manufactured by the manufacturing method of the invention is the individual package 1 formed in such a manner that the tampon with applicator 3 having the applicator 4 with the external cylinder 40 and the internal cylinder 41 and the absorbent body 30 housed so as to be pushed out from the applicator 4 is individually enclosed in the flat package bag 2 which is formed by the package sheet 21 which is a predetermined sheet member.

As shown in FIG. 19A, in the perforated line forming step, a perforated line is formed at a predetermined position of the long package sheet 21 such that the package sheet 21 can be separated, for example, by perforated line cutting means such as a predetermined laser apparatus. As the perforated line cutting means, in addition to the laser apparatus, a rolly cutter or the like with a blade of a perforated line can be also used.

As shown in FIG. 19B, in the graspable portion forming step, the graspable portion 28 is formed by folding the package sheet 21 into a sailor. Specifically, a valley-folded portion 51 of the package sheet 21 is folded down into a rear surface side. Subsequently, a mountain-folded portion 52 of the package sheet 21 is folded down into a surface side. In this manner, the valley-folded portion 51 and the mountain-folded portion 52 are folded back into predetermined directions, respectively, to thereby form the graspable portion 28. In the lid portion forming step, the graspable portion 28 formed by the graspable portion forming step is further folded down to the surface side. Thereby, the package sheet 21 is formed into the flat shape with respective surfaces facing each other and the lid portion 24 is formed on the surface side.

As shown in FIG. 19C, the joining step joins the opposing ends of the folded package sheet 21 in the longitudinal direction. Specifically, the portion from the rear end in the longitudinal direction up to the position of forming a perforated line is joined. Consequently, the housing portion 25 (bag) of the package bag 2 is formed. Subsequently, the opposing sides of the lid portion 24 in the longitudinal direction are joined. In this case, the lid portion 24 is joined so as to be detachable.

According to the sealed portion forming step, predetermined positions on the opposing sides in the longitudinal direction of surfaces facing each other, of the housing portion 25 formed in the flat bag are joined into predetermined shapes. Thereby, the sealed portion 26 is formed.

As shown in FIG. 19D, according to the tampon inserting step, the tampon with applicator 3 is inserted in the bag which is the housing portion 25 formed by the sealed portion joining step.

As shown in FIG. 19E, in the opening bonding step, the opening on the lower end 53 of the bag in which the tampon with applicator 3 has been inserted by the tampon inserting step is joined, and the tampon with applicator 3 is enclosed therein. Thereby, the individual package 1 is formed.

Manufacturing System

In the case of industrially manufacturing the individual package according to the invention, for example, the following manufacturing system can be used.

The invention provides a manufacturing system for an individual package 1 formed with a tampon 3 comprising an applicator 4 having an external cylinder 40 and an internal cylinder 41 and an absorbent body 30 housed so as to be pushed out from the applicator 4 is individually enclosed in an elongate package bag 2 which is formed by a predetermined sheet-member 200. As shown in FIGS. 20 and 21, the manufacturing system includes sheet supply means 100 for supplying a sheet-like package material 200 in a fixed direction; perforated line forming means 101 for forming a perforated line 201 at a predetermined position of the sheet-like package material 200 supplied by the sheet supply means 100; graspable portion forming means 102 for forming a graspable portion 28 at a predetermined position by folding a part 202 of the sheet-like package material 200; folding back means 103 for folding back the sheet-like package material 200 at a predetermined position 203; bonding means 104 for bonding at least a part in a width direction of the sheet-like package material 200 folded back by the folding back means 103 at predetermined intervals; sealed portion forming means 105 for forming a sealed portion 26 formed in a predetermined shape; separating means 106 for separating the sheet-like package material 200 bonded by the bonding means 104 at predetermined intervals; tampon inserting means 107 for inserting the tampon with applicator 3 in an opening; and opening joining means 108 for joining the opening 208.

The sheet supply means 100 supplies the predetermined sheet-like package material 200 rolled by, for example, a drum in a predetermined direction at a predetermined rate. For example, the sheet-like package material 200 is supplied in a state as shown in A of FIG. 20. The predetermined sheet-like package material 200 may include a sheet-like package material having the rear surface or the front surface applied with the embossing process. In this case, an embossing process step (not shown) may be provided.

For example, as shown in B of FIG. 20, the perforated line forming means 101 forms the perforated line 201 at a predetermined position equivalent to the unsealable portion 22 so as to be unsealable by a predetermined cutter or the like. For example, a laser apparatus ($CO_2$ LASER MARKER ML-G930, manufactured by Keyence Corporation) can be used as the cutter. Examples of the perforated line forming means include not only the laser apparatus, but also a rolly-cutter with a blade of a perforated line.

For example, as shown in C of FIG. 20, The graspable portion forming means 102 forms the graspable portion 28 by folding the sheet-like package material 200. Specifically, the sheet-like package material 200 is folded down into the rear surface side on a valley-folded portion 202a thereof. Then, the sheet-like package material 200 is folded down into the surface side on a mountain-folded portion 202b thereof. Thus, the valley-folded portion 202a and the mountain-folded portion 202b are folded down in predetermined directions, respectively, to thereby form the graspable portion 28.

The folding down means 103, for example, as shown in D of FIG. 20, further folds down a part of the sheet-like package material 200 including the graspable portion 28 formed by the graspable portion forming means 102 to the surface side. As a consequence, the sheet-like package material 200 is formed into the substantially flat shape. The folding down means 103 can be formed, for example, by using double-folding means (not shown).

For example, as shown in E of FIG. 20, the bonding means 104 bonds the interior part of the surface which becomes the inside upon manufacturing of the sheet-like package material 200, namely, a region 204 which is equivalent to the bonded sides 23 by means of a heat sealing process or the like. In addition, a region 205 which is equivalent to the lid portion bonding portion 27 is bonded by blowing an adhesive due to a hot melt process or the like. The bonding means may be means capable of bonding the sheet-like package material 200. For example, the bonding means may be a fusion bonding, a pressure bonding or the like. In addition, the bonding means may involve the embossing process. Thereby, the sheet-like package material is formed into a bag shape having an opened rear end.

The sealed portion forming means 105 (not shown) joins a part of the sheet-like package material 200 into a predetermined shape on the region 204 which is equivalent to the bonded sides 23. Joining may be the same as the bonding means 104.

For example, as shown in F of FIG. 20, the separating means 106 separates the sheet-like package materials 200 at a predetermined position 206 at predetermined intervals so as to form individual package sheet 21.

For example, as shown in G of FIG. 20, the tampon inserting means 107 opens the opening 208 on the lower end 53 of the package sheet 21 formed into a bag shape so as to insert the tampon with applicator 3 from the opening 208. In this case, the tampon with applicator 3 is inserted from a direction of the internal cylinder 41 of the applicator 4.

For example, as shown in H of FIG. 20, the opening joining means 108 joins the opening 208 of the package bag 2 having the tampon with applicator 3 inserted thereinto so as to enclose the tampon with applicator 3 in the package bag 2. Thereby, the individual package 1 is completed. The manufacturing system is provided with various guide rollers.

FIG. 22 shows a manufacturing system for an individual package 1C which is the forth embodiment when a surface side sheet-like package material 300 and a rear surface side sheet-like package material 302 are used, respectively. As shown in FIG. 22, first, the surface side sheet-like package material 300 is obliquely cut at a predetermined position 301 in a perforated line by means of the cutting means. Next, by combining the surface side sheet-like package material 300 and the rear surface side sheet-like package material 302, the surface side sheet-like package material 300 and the rear surface side sheet-like package material 302 are joined by the joining means at a region 304 which is equivalent to the housing portion 25.

Further, the adhesive due to the hot melt process or the like is blown to a predetermined position of the rear surface side sheet-like package material 302. Then, a folded-back portion 305 is folded down by the folding back means. As the folding back means, the folding back sailor means may be used, for example.

Next, a region 306 which is equivalent to the lid portion bonding portions 27 is bonded by the joining means. Further, by the separating means, the surface side sheet-like package material 300 and the rear surface side sheet-like package material 302 are separated at predetermined intervals at a predetermined position 307 so as to form individual package sheet 21.

By opening an opening 309 on the lower end of the package sheet 21 formed in a bag shape by the tampon inserting means, the tampon with applicator 3 is inserted from the opening 309. In this case, the tampon with applicator 3 is inserted from a direction of the internal cylinder 41 of the applicator 4.

By use of the opening joining means, the opening 309 of the package bag 2 having the tampon with applicator 3 inserted thereinto is joined so as to enclose the tampon with applicator 3 in the package bag 2. Consequently, the individual package 1C is completed.

According to the individual package 1, there are provided the unsealable portion 22 formed on one side of the flat shape of the package bag 2 so as to allow the tampon with applicator 3 to be removed therefrom and the lid portion 24 which is openable and closable in the longitudinal direction of the package bag 2, thereby obtaining a clearance of the unsealable portion 22 having a stable predetermined opening shape. In addition, since the unsealable portion 22 is covered with the lid portion 24, the lid portion 24 is lifted up on the unsealable portion 22 and the position of the unseablle portion 22 is easily found. For example, in the case of forming the unsealable portion 22 into a mountain shape, the clearance of the unsealable portion 22 is easily widened, so that the used applicator 4 can be easily inserted. By providing the lid portion 24, the lid can be closed after housing the used applicator 4. This makes it possible to keep the unsealed package bag 2 clean. Further, for example, by bonding the lid portion 24 by the bonding means capable of rebonding, the lid portion 24 can be bonded again even after opening the lid portion 24. This makes it possible to keep the unsealed package bag 2 clean.

According to the individual package 1, the unsealable portion 22 is formed to be continued to the lid portion 24 and is formed into a perforated shape to allow itself to be separated from the lid portion 24. Thereby, the unsealable portion 22 is unsealed by the unsealing operation toward the longitudinal direction of the lid portion 24. Further, the unsealable portion 22 formed in the perforated shape is covered with the lid portion 24 and the clearance of the unseaable portion 22 is not opened till the perforated line is broken. For this reason, the tampon with applicator 3 enclosed in the package bag 2 does not directly contact air and can be kept clean.

According to the individual package 1, the lid portion 24 has the graspable portion 28 integrally formed therewith. With this configuration, it is possible to unseal the package bag 2 by using the graspable portion 28 upon unsealing, so that the package bag 2 can be easily unsealed. Here, the term "integrally formed" includes the case of using a part of the lid portion 24 as the graspable portion 28, for example. The graspable portion 28 may be formed by folding back the package bag 2 forming the lid portion 24. By forming the graspable portion 28 by folding back the package bag 2 in this way, the graspable portion 28 is lifted up to be formed in three dimensions. This makes it possible for the user to more easily know the unsealable portion 22.

According to the individual package 1, the package bag 2 has a surface, which forms the inside of the housing portion 25 for housing the tampon with applicator 3, applied with the unevening process, for example, embossing process. As a consequence, a contact area between the package sheets 21 forming the package bag 2 is reduced, which leads to the advantage that the package sheets 21 hardly stick and easily unstuck. In addition, the surface of the sheet member is uneven, which causes a difference in bending resistance of the package sheet 21. That is, a relatively soft part and a relatively rigid part are generated. Consequently, the soft part receives a force from the rigid part, so that the package sheet 21 is easily bent. As a result, the package bag 2 can be easily unsealed and a predetermined spacious portion can be easily formed upon unsealing the bag.

The embossing process may be applied on the surface of the package sheet 21 forming the package bag 2. In other words, the unevening process may be applied at least on the inner surface of the package bag 2, or the unevening process may be applied on the inner surface and the surface of the package bag 2. By applying the unevening process on the surface of the package bag 2, a slip stopper is provided upon unsealing.

According to the individual package 1, by providing the sealed portion 26 on the side of the package bag 2, the joined package sheets 21 to be integrated, so that the rigidity of the sealed portion 26 is increased. Therefore, the package sheets 21 on the sealed portion 26 do not move well, and as compared to the width of the clearance of the unsealable portion 22, a movable range of the package sheet 21 on the sealed portion 26 becomes narrow. Due to such a difference in the movable range of the package sheet 21, wide ruck generated when the package sheets 21 are slid is generated on the unsealable portion. This allows a space to be easily generated on the opening. With this configuration, the applicator 4 after usage of the tampon can be easily put in the package bag 2 with a space generated on the clearance. In addition, since the sealed portion 26 can be used also as a handle, which enables the individual package to be easily treated.

According to the individual package 1, the sealed portion 26 is formed so as to project in a substantially semicircular shape in a longitudinal direction of the package bag 2. In other words, the corner of the sealed portion 26 is chamfered so that the sealed portion 26 has no angular part. Thereby, the following advantage is achieved. That is, assume that, for example, in the case of inserting the applicator 4 or the tampon with applicator 3 into the package bag 2, the internal cylinder 41 or the external cylinder 40 of the applicator 4 abuts against the sealed portion 26. Even in this case, it is possible to immediately insert the applicator 4 or the tampon with applicator 3 inside of the package bag 2 without jamming because the process for chamfering the angular portions is applied. Moreover, in the case where the sealed portions 26 are formed on the opposing sides of the package bag 2, the applicator 4 or the tampon with applicator 3 can be stabilized because the sealed portions 26 guide the applicator 4 or the tampon with applicator 3 to a substantially center part of the package bag 2.

According to the individual package 1, the unsealable portion 22 is formed so as to have a predetermined angle with a hypothetical line L extending in the longitudinal direction of the package bag 2. In other words, the unsealable portion 22 is formed in an oblique direction with respect to the hypothetical line L extending in the longitudinal direction. With this configuration, the clearance of the unsealable portion 22 can be increased. In addition, respective sealed portions 26 are provided so as to be separated from each other such that the inclined angles in a width direction formed by a hypothetical line P combining the respective sealed portions 26 make the same angles with the unsealable portion 22. Consequently, upon unsealing the unsealable portion 22, for example, a force is easily transmitted to the unsealable portion 22. This makes it possible to easily unseal the package bag 2.

According to the individual package 1, the length of the package bag 2 in the width direction is made longer than the maximum outer diameter of the external cylinder 40 of the applicator 4. Specifically, the length of the package bag 2 in the width direction is formed in the range of 180% to 320% of the maximum outer diameter. Accordingly, the length of the package bag 2 in the width direction is longer than the outline of the applicator 4. With this configuration, the clearance of the unsealable portion 22 is increased, which allows the used applicator 4 to be easily put into the package bag 2. Further, it is difficult for the body fluid or the like adhering to the applicator 4 to adhere to the vicinity of the unsealable portion 22 of the package bag 2. Accordingly, it becomes easy to insert the used applicator 4 into the unsealed package bag 2, and the applicator 4 can be smoothly discarded without soiling a hand.

While preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention. Accordingly, the invention is not to be considered to be limited by the foregoing description and is only limited by the scope of the appended claims.

What is claimed is:

1. An individual package comprising a tampon and a flat bag;
   the tampon comprises:
      an applicator having an external cylinder and an internal cylinder; and
      an absorbent body housed so as to be pushed out from the applicator, the tampon being individually enclosed in the flat bag formed with a predetermined sheet member in an elongated shape,
   the flat bag comprises:
      an unsealable portion formed as a perforated line on a first face of the flat bag extending in a width direction of the flat bag, so as to enable the tampon to be removed therefrom, the perforated line being formed so as to create a line that may be torn to open the bag;
      a lid portion provided on the first face of the flat bag so as to be openable and closable in a longitudinal direction of the flat bag, the unsealable portion being covered with the lid portion, said lid portion including a z-folded portion that covers the unsealable portion;
      a folded-back portion formed by folding the sheet member at one longitudinal end of the flat bag; and
      a bottom bonded portion at another longitudinal end of the flat bag into which the tampon is inserted, wherein the first face of the flat bag and a second face of the flat bag opposed to the first face of the flat bag are attached to each other at the bottom bonded portion.

2. The individual package according to claim 1, wherein the lid portion is formed continuously along the unsealable portion, and
   the unsealable portion is formed in a perforated shape which allows the lid portion to be separated therefrom.

3. The individual package according to claim 1, wherein the lid portion has a graspable portion integrally formed therewith.

4. The individual package according to claims 1, wherein the flat bag is applied with unevening process on its inner surface.

5. The individual package according to claim 1, wherein the flat bag includes a sealed portion which is formed on the side of the flat bag in the longitudinal direction, so as to project to the inside of the flat bag, the sealed portion being formed by joining one sheet member and another sheet member facing each other.

6. The individual package according to claim 5, wherein the sealed portion is formed in a substantially semicircular shape.

7. The individual package according to claim 5, wherein the unsealable portion is formed along a traversing line across a width direction of the flat bag so as to have a predetermined angle with a hypothetical line extending in the longitudinal direction of the flat bag, and the sealed portions are provided on the opposing sides of the flat bag, respectively, and are formed such that a hypothetical line combining the respective sealed portions is parallel with the traversing line.

8. The individual package according to claim 1, wherein a length of the flat bag in a width direction is in the range of 180% or more of the maximum diameter of the applicator.

9. The individual package according to claim 1, wherein the predetermined sheet member comprises a continuous sheet member detached at the unsealed portion along the perforated line extending in the width direction of the flat bag.

* * * * *